(12) United States Patent
Uhlén et al.

(10) Patent No.: US 8,241,859 B2
(45) Date of Patent: Aug. 14, 2012

(54) USE OF PROTEIN SATB2 AS A MARKER FOR COLORECTAL CANCER

(75) Inventors: Mathias Uhlén, Stocksund (SE); Fredrik Pontén, Uppsala (SE)

(73) Assignee: Atlas Antibodies AB, Stockholm (SE)

( * ) Notice: Subject to any disclaimer, the term of this patent is extended or adjusted under 35 U.S.C. 154(b) by 0 days.

(21) Appl. No.: 13/278,473

(22) Filed: Oct. 21, 2011

(65) Prior Publication Data

US 2012/0028836 A1    Feb. 2, 2012

Related U.S. Application Data

(63) Continuation of application No. 12/302,248, filed as application No. PCT/EP2007/004931 on Jun. 4, 2007, now Pat. No. 8,067,190.

(60) Provisional application No. 60/816,613, filed on Jun. 27, 2006.

(30) Foreign Application Priority Data

Jun. 2, 2006  (EP) .................................. 06114954

(51) Int. Cl.
   *G01N 33/53*  (2006.01)
   *G01N 33/574*  (2006.01)
(52) U.S. Cl. ........................................ 435/7.1; 435/7.23
(58) Field of Classification Search ........................ None
See application file for complete search history.

(56) References Cited

U.S. PATENT DOCUMENTS

| 2003/0129207 A1* | 7/2003 | Meagher et al. ........... 424/277.1 |
| 2008/0311567 A1* | 12/2008 | Bruckl et al. ..................... 435/6 |
| 2009/0270267 A1 | 10/2009 | Akiyama et al. |

FOREIGN PATENT DOCUMENTS

| EP | 1862803 A1 | 12/2007 |
| GB | 2435882 A | 9/2007 |
| WO | WO 00/40752 A2 | 7/2000 |
| WO | WO 03/022126 A2 | 3/2003 |
| WO | WO 2005/107396 A2 | 11/2005 |
| WO | WO 2006/015742 A2 | 2/2006 |

OTHER PUBLICATIONS

Wang et al (Journal of Pathology, 2009, 219:114-122, IDS).*
Agaton et al., "Genome-based proteomics", Electrophoresis, vol. 25, 2004, pp. 1280-1288.
Andersson et al., "Analysis of Protien Expression in Cell Microarrays: A Tool for Antibody-based Proteomics", Journal of Histochemistry & Cytochemistry, vol. 54, No. 12, 2006, pp. 1413-1423.
AU Office Action, Appl. No. 2007256391, Jan. 20, 2011, pp. 1-4.
Bode et al., "Transcriptional Augmentation: Modulation of Gene Expression by Scaffold/Matrix Attached Regions (S/MAR Elements)", Crit Rev Eukaryot Gene Expr., vol. 10, No. 1, 2000, 26 pages.
Britanova et al., "Novel transcription factor Satb2 interacts with matrix attachment region DNA elements in a tissue-specific manner and demonstrates cell-type-dependent expression in the developing mouse CNS", European Journal of Neuroscience, vol. 21, 2005, pp. 658-668.
Cheng et al., "The clinical implications of MMP-11 and CK-20 expression in human breast cancer", Clinica Chimica Acta, vol. 411, 2010, pp. 234-241 (Available online Nov. 13, 2009).
Chung et al., "SATB2 augments ?Np63a in head and neck squamous cell carcinoma", EMBO reports, Published Online Sep. 10, 2010, p. 1-7.
Dickinson et al., "A Tissue-Specific MAR/SAR DNA-Binding Protein with Unusual Binding Site Recognition", Cell, vol. 70, Aug. 21, 1992, pp. 631-645.
Dobreva et al., "SUMO modification of a novel MAR-binding protein, SATB2, modulates immunoglobulin μ gene expression", Genes & Developement, vol. 17, 2003, pp. 3048-3061.
EPO Office Action, Appl. No. 07725799.6, Mar. 1, 2010, pp. 1-4.
EPO Search Report, Appl. No. 10158956.2, Jun. 25, 2010, pp. 1-8.
Extended European Search Report dated Mar. 10, 2009, for Application No. 08165897.3.
Fitzpatrick et al., "Identification of SATB2 as the cleft palate gene on 2q32-q33", Human Molecular Genetics, vol. 12, No. 19, 2003, pp. 2491-2501.
Giribaldi et al., "Specific Detection of Cytokeratin 20-Positive Cells in Blood of Colorectal and Breast Cancer Patients by a High Sensitivity Real-Time Reverse Transcriptase-Polymerase Chain Reaction Method", Journal of Molecular Diagnostics, vol. 8, No. 1, Feb. 2006, pp. 105-112.
Groene et al., "Transcriptional census of 36 microdissected colorectal cancers yields a gene signature to distinguish UICC II and III", International Journal of Cancer, vol. 119, 2006, pp. 1829-1836 (Published online May 23, 2006).
Kampf et al., "Antibody-Based Tissue Profiling As a Tool for Clinical Proteomics", Clinical Proteomics Journal, vol. 1, 2004, pp. 285-299.
Kikuno et al., "Prediction of the Coding Sequences of Unidentified Human Genes. XIV. The Complete Sequences of 100 New cDNA Clones from Brain Which Code for Large Proteins in vitro", DNA Research, vol. 6, 1999, pp. 197-205.
Kummar et al., "Cytokeratin 7 and 20 staining for the diagnosis of lung and colorectal adenocarcinoma", British Journal of Cancer, vol. 86, 2002, pp. 1884-1887.
Lindskog et al., "Selection of protein epitopes for antibody production", BioTechniques, vol. 38, No. 5, May 2005, pp. 723-727. Pasche et al., "Molecular markers in prognosis of colorectal cancer and prediction of response to treatment", Best Practice & Research Clinical Gastroenterology, vol. 16, No. 2, 2002, pp. 331-345, XP-002447570.
Patani et al., "The mRNA expression of SATB1 and SATB2 in human breast cancer", Cancer Cell International, vol. 9, No. 18, Jul. 30, 2009, 10 pages.
PCT International Preliminary Report on Patentability and Written Opinion of the International Searching Authority,dated Apr. 12, 2011, for Application No. PCT/EP2009/062956.
Rockberg et al., "Epitope mapping of antibodies using bacterial surface display", Nature Methods, Dec. 2008, vol. 5, No. 12, pp. 1039-1045.
Salahshor et al., "Differential gene expression profile reveals deregulation of pregnancy specific βI glycoprotein 9 early during colorectal carcinogenesis", BMC Cancer, vol. 5, No. 66, Jun. 27, 2005, 14 pages.
Soong et al., "Quantitative Reverse Transcription-Polymerase Chain Reaction Detection of Cytokeratin 20 in Noncolorectal Lymph Nodes", Clinical Cancer Research, vol. 7, Nov. 2001, pp. 3423-3429.
Tot, "Cytokeratins 20 and 7 as biomarkers: usefulness in discriminating primary from metastatic adenocarcinoma," European Journal of Cancer, vol. 38, 2002, pp. 758-763.

(Continued)

*Primary Examiner* — Laura B Goddard
(74) *Attorney, Agent, or Firm* — Birch, Stewart, Kolasch & Birch, LLP

(57) ABSTRACT

The invention provides new methods, means and uses in connection with detection, characterization and prognosis of colo-rectal cancer, via the identification of the SATB2 protein as a marker for this cancer type.

26 Claims, 16 Drawing Sheets

OTHER PUBLICATIONS

Uhlen et al., "A Human Protein Atlas for Normal and Cancer Tissues Based on Antibody Proteomics", Molecular & Cellular Proteomics, vol. 4, No. 12, Aug. 27, 2005, pp. 1920-1932.

Uhlen et al., "Antibody-based Proteomics for Human Tissue Profiling", Molecular & Cellular Proteomics vol. 4, No. 4, 2005, pp. 384-393.

Van Buggenhout et al., "The del(2)(q32.2q33) deletion syndrome defined by clinical and molecular characterization of four patients", European Journal of Medical Genetics, vol. 48, 2005, pp. 276-289 (Available Online Jun. 6, 2005).

Wang et al., "Down-regulated expression of SATB2 is associated with the metastasis and poor prognosis in colorectal cancer", Journal of Pathology, vol. 219, 2009, pp. 114-122 (Published online May 8, 2009).

Yasui et al., "SATB1 targets chromatin remodelling to regulate genes over long distances", Nature, vol. 419, Oct. 10, 2002, pp. 641-645.

Chinese First Office Action for Appl. No. 200780020492.9 dated Apr. 5, 2012.

* cited by examiner

| | | SATB2 Nuclear fraction | | | | |
|---|---|---|---|---|---|---|
| | | 0-1% | 2-25% | 26-75% | >75% | total |
| CK 20 Nuclear fraction | 0-1% | 5 | 1 | 4 | 7 | 17 |
| | 2-25% | 3 | | 5 | 12 | 20 |
| | 26-75% | 4 | 1 | 6 | 21 | 32 |
| | >75% | 11 | 3 | 16 | 23 | 53 |
| | total | 23 | 5 | 31 | 63 | 122 |

FIGURE 8

Satb2 vs CK20 in lymph nodes

| Count | | Satb2 nuclear fraction | | | Total |
|---|---|---|---|---|---|
| | | 0-1% | 26-75% | >75% | |
| CK20 nuclear fraction | 0 | 1 | | | 1 |
| | 1 | | | 1 | 1 |
| | 2 | 1 | 2 | 3 | 6 |
| | 3 | 1 | 3 | 5 | 9 |
| Total | | 3 | 5 | 9 | 17 |

FIGURE 9

SEQUENCE LISTING

<160> NUMBER OF SEQ ID NOS: 5

<210> SEQ ID NO 1
<211> LENGTH: 123
<212> TYPE: PRT
<213> ORGANISM: Homo sapiens

<400> SEQUENCE: 1

Val Ser Gln Ala Val Phe Ala Arg Val Ala Phe Asn Arg Thr Gln Gly
1               5                   10                  15

Leu Leu Ser Glu Ile Leu Arg Lys Glu Glu Asp Pro Arg Thr Ala Ser
            20                  25                  30

Gln Ser Leu Leu Val Asn Leu Arg Ala Met Gln Asn Phe Leu Asn Leu
        35                  40                  45

Pro Glu Val Glu Arg Asp Arg Ile Tyr Gln Asp Glu Arg Glu Arg Ser
    50                  55                  60

Met Asn Pro Asn Val Ser Met Val Ser Ser Ala Ser Ser Ser Pro Ser
65                  70                  75                  80

Ser Ser Arg Thr Pro Gln Ala Lys Thr Ser Thr Pro Thr Thr Asp Leu
            85                  90                  95

```
Pro Ile Lys Val Asp Gly Ala Asn Ile Asn Ile Thr Ala Ala Ile Tyr
            100                 105                 110

Asp Glu Ile Gln Gln Glu Met Lys Arg Ala Lys
            115                 120

<210> SEQ ID NO 2
<211> LENGTH: 733
<212> TYPE: PRT
<213> ORGANISM: Homo sapiens

<400> SEQUENCE: 2

Met Glu Arg Arg Ser Glu Ser Pro Cys Leu Arg Asp Ser Pro Asp Arg
 1               5                  10                  15

Arg Ser Gly Ser Pro Asp Val Lys Gly Pro Pro Val Lys Val Ala
             20                  25                  30

Arg Leu Glu Gln Asn Gly Ser Pro Met Gly Ala Arg Gly Arg Pro Asn
         35                  40                  45

Gly Ala Val Ala Lys Ala Val Gly Gly Leu Met Ile Pro Val Phe Cys
 50                  55                  60

Val Val Glu Gln Leu Asp Gly Ser Leu Glu Tyr Asp Asn Arg Glu Glu
65                  70                  75                  80

His Ala Glu Phe Val Leu Val Arg Lys Asp Val Leu Phe Ser Gln Leu
                 85                  90                  95

Val Glu Thr Ala Leu Leu Ala Leu Gly Tyr Ser His Ser Ser Ala Ala
            100                 105                 110

Gln Ala Gln Gly Ile Ile Lys Leu Gly Arg Trp Asn Pro Leu Pro Leu
        115                 120                 125

Ser Tyr Val Thr Asp Ala Pro Asp Ala Thr Val Ala Asp Met Leu Gln
130                 135                 140

Asp Val Tyr His Val Val Thr Leu Lys Ile Gln Leu Gln Ser Cys Ser
145                 150                 155                 160

Lys Leu Glu Asp Leu Pro Ala Glu Gln Trp Asn His Ala Thr Val Arg
                165                 170                 175

Asn Ala Leu Lys Glu Leu Leu Lys Glu Met Asn Gln Ser Thr Leu Ala
            180                 185                 190

Lys Glu Cys Pro Leu Ser Gln Ser Met Ile Ser Ser Ile Val Asn Ser
        195                 200                 205

Thr Tyr Tyr Ala Asn Val Ser Ala Thr Lys Cys Gln Glu Phe Gly Arg
210                 215                 220

Trp Tyr Lys Lys Tyr Lys Lys Ile Lys Val Glu Arg Val Glu Arg Glu
225                 230                 235                 240

Asn Leu Ser Asp Tyr Cys Val Leu Gly Gln Arg Pro Met His Leu Pro
                245                 250                 255

Asn Met Asn Gln Leu Ala Ser Leu Gly Lys Thr Asn Glu Gln Ser Pro
            260                 265                 270

His Ser Gln Ile His His Ser Thr Pro Ile Arg Asn Gln Val Pro Ala
        275                 280                 285

Leu Gln Pro Ile Met Ser Pro Gly Leu Leu Ser Pro Gln Leu Ser Pro
290                 295                 300

Gln Leu Val Arg Gln Gln Ile Ala Met Ala His Leu Ile Asn Gln Gln
305                 310                 315                 320

Ile Ala Val Ser Arg Leu Leu Ala His Gln His Pro Gln Ala Ile Asn
                325                 330                 335

Gln Gln Phe Leu Asn His Pro Pro Ile Pro Arg Ala Val Lys Pro Glu
            340                 345                 350
```

-continued

Pro Thr Asn Ser Ser Val Glu Val Ser Pro Asp Ile Tyr Gln Gln Val
            355                 360                 365

Arg Asp Glu Leu Lys Arg Ala Ser Val Ser Gln Ala Val Phe Ala Arg
    370                 375                 380

Val Ala Phe Asn Arg Thr Gln Gly Leu Leu Ser Glu Ile Leu Arg Lys
385                 390                 395                 400

Glu Glu Asp Pro Arg Thr Ala Ser Gln Ser Leu Leu Val Asn Leu Arg
                405                 410                 415

Ala Met Gln Asn Phe Leu Asn Leu Pro Glu Val Glu Arg Asp Arg Ile
            420                 425                 430

Tyr Gln Asp Glu Arg Glu Arg Ser Met Asn Pro Asn Val Ser Met Val
        435                 440                 445

Ser Ser Ala Ser Ser Ser Pro Ser Ser Ser Arg Thr Pro Gln Ala Lys
    450                 455                 460

Thr Ser Thr Pro Thr Thr Asp Leu Pro Ile Lys Val Asp Gly Ala Asn
465                 470                 475                 480

Ile Asn Ile Thr Ala Ala Ile Tyr Asp Glu Ile Gln Gln Glu Met Lys
                485                 490                 495

Arg Ala Lys Val Ser Gln Ala Leu Phe Ala Lys Val Ala Ala Asn Lys
            500                 505                 510

Ser Gln Gly Trp Leu Cys Glu Leu Leu Arg Trp Lys Glu Asn Pro Ser
    515                 520                 525

Pro Glu Asn Arg Thr Leu Trp Glu Asn Leu Cys Thr Ile Arg Arg Phe
    530                 535                 540

Leu Asn Leu Pro Gln His Glu Arg Asp Val Ile Tyr Glu Glu Glu Ser
545                 550                 555                 560

Arg His His His Ser Glu Arg Met Gln His Val Val Gln Leu Pro Pro
                565                 570                 575

Glu Pro Val Gln Val Leu His Arg Gln Gln Ser Gln Pro Ala Lys Glu
            580                 585                 590

Ser Ser Pro Pro Arg Glu Glu Ala Pro Pro Pro Pro Pro Thr Glu
    595                 600                 605

Asp Ser Cys Ala Lys Lys Pro Arg Ser Arg Thr Lys Ile Ser Leu Glu
    610                 615                 620

Ala Leu Gly Ile Leu Gln Ser Phe Ile His Asp Val Gly Leu Tyr Pro
625                 630                 635                 640

Asp Gln Glu Ala Ile His Thr Leu Ser Ala Gln Leu Asp Leu Pro Lys
                645                 650                 655

His Thr Ile Ile Lys Phe Phe Gln Asn Gln Arg Tyr His Val Lys His
            660                 665                 670

His Gly Lys Leu Lys Glu His Leu Gly Ser Ala Val Asp Val Ala Glu
    675                 680                 685

Tyr Lys Asp Glu Glu Leu Leu Thr Glu Ser Glu Asn Asp Ser Glu
    690                 695                 700

Glu Gly Ser Glu Glu Met Tyr Lys Val Glu Ala Glu Glu Asn Ala
705                 710                 715                 720

Asp Lys Ser Lys Ala Ala Pro Ala Glu Ile Asp Gln Arg
                725                 730

<210> SEQ ID NO 3
<211> LENGTH: 5318
<212> TYPE: DNA
<213> ORGANISM: Homo sapiens

<400> SEQUENCE: 3

```
gagagagaga gagagagact gagaaagtcg aactcgagct taggtaacca acaaacccaa      60
ttactaggct ttattgatac taaaaggaaa agttcccctc gtaaaatttc tctgagctta     120
ttagttattt aaatcagccc cagggttgga cgcgtgacgc cgaaggcacc ttctgtcggc     180
tcctggaggt gagcagccag cgtccctgcg ccgacccaca gcccctcgct ccgtcctggg     240 cacttgggc gaaggcgggc gcagcgagcc gagaagtact gaactcctaa tatccaccaat    300 tcttctaagt tcctggacat tgatccggag gaggattcgc agttcaacat caaggtccct     360
gtgcgtttta ttgcgacctg ccggtgggaa ctttgtctcc gagtcggagc agcatggagc     420
ggcggagcga gagcccgtgt ctgcgggaca gccccgaccg gcggagcggc agcccggacg     480
tcaaggggcc tcccccagtg aaggtggccc ggctggagca aacggcagc cccatgggag      540 cccgcgggag gcccaacggc gccgtggcca aggccgtggg aggtttgatg attcctgtct     600
tttgtgtcgt ggagcagttg gacggctctc ttgaatatga caacagagaa gaacacgccg     660
agtttgtcct ggtgcggaaa gatgtgcttt ttagccagct ggtggagact gcgctcctgg     720
ccctggggta ttctcacagc tctgcggccc aggcccaagg aataatcaag ctgggaaggt     780
ggaaccctct ccccctcagt tatgtgacag atgcacccga cgcgacagtg gccgacatgc     840
tacaagatgt ctatcatgtt gtgacgttga aaatccaatt acaaagttgt tcaaagttgg     900
aagacttgcc tgcggagcag tggaaccatg ccacagtccg caatgcctta aaggaactgc     960
tcaaagagat gaaccagagc acattagcca agaatgccc tctctcccag agtatgattt    1020
catccattgt aaatagcaca tattatgcca atgtgtcagc aaccaagtgc caggagtttg    1080
ggagatggta taaaaagtac aagaagatta agtggaaag agtggaacga gaaaaccttt     1140
cagactattg tgttctgggc cagcgtccaa tgcatttacc aaatatgaac cagctggcat    1200
ccctggggaa aaccaacgaa cagtctcctc acagccaaat tcaccacagt actccaatcc    1260
gaaaccaagt gcccgcatta cagcccatca tgagccctgg tcttctttct ccccagctta    1320
gtccacaact tgtaaggcaa caaatagcca tggcccatct gataaaccaa cagattgccg    1380
ttagccggct cctggctcac cagcatcctc aagccatcaa ccagcagttc ctgaaccatc    1440
cacccatccc cagagcagtt aagccagagc caaccaactc ttccgtggaa gtctctccag    1500
atatctacca gcaagtcaga gatgagctga agagggccag tgtgtcccaa gctgtctttg    1560
caagagtggc attcaaccgc acacagggat tgttgtctga gattctgcgt aaggaagaag    1620
accctcggac agcctctcag tctcttctag taaacctgag ggccatgcag aatttcctca    1680
atctgccaga agtggagcga gatcgcatct accaggatga gagggagcgg agcatgaatc    1740
ccaatgtgag catggtctcc tcggcctcca gcagtcccag ctcctcccga accccctcagg   1800 ccaaaacctc gacaccgaca acagacctcc ctattaaggt ggacggcgcc aacatcaaca    1860
tcacagctgc catttatgac gagatccaac aggagatgaa aagggccaag gtgtctcaag    1920
ccctgtttgc caagtggct gcaaataaaa gtcagggctg gctgtgtgaa ctgctccgct     1980
ggaaggagaa cccaagccca gaaaccgca ccctctggga aaacctctgt accatccgtc     2040
gcttcctgaa ccttccccag catgagaggg atgtcatcta tgaggaggag tcaaggcatc    2100
accacagcga acgcatgcaa cacgtggtcc agcttccccc tgagccggtg caggtacttc    2160
atagacagca gtctcagcca gccaaggaga gttcccctcc cagagaagaa gcgcctcccc    2220
cacctcctcc gactgaagac agttgtgcca aaaagcccg gtctcgcaca aagatctcct    2280
tagaagccct ggggatcctc caaagcttta ttcatgatgt aggcctgtac ccagaccagg    2340
aagccatcca cactctttcg gctcagctgg atctccccaa acacaccatc atcaagttct   2400
```

```
tccagaacca gcggtaccac gtgaagcacc acgggaagct gaaagagcac ctgggctccg    2460
cggtggacgt ggctgaatat aaggacgagg agctgctgac cgagtcagag gagaacgaca    2520
gcgaggaagg ctccgaggag atgtacaaag tggaggctga ggaggaaaat gctgacaaaa    2580
gcaaggcagc acctgccgaa attgaccaga gataatgtga acttctacta ggcaaagcaa    2640
tacatcggtc caaggatttt ctgctttcat ttctttaaaa gttttttgtt agtttgtttt    2700 ttgttttttgt ttttgggttt tttggctttt attttttgtct tttatgtct gttttgtttt   2760 tcttacccctt ttggacattt ctttgttgca caggatacac ctatagactg aataagttca   2820
gtatttccga atcagacatc gccttggcaa agacactaaa gcgttacact ttatcccgtc    2880
tctatgactg gatcatagtc attataatca caggagactc tgccttcatt atccttgcac    2940
ttaacggaag ttacatcagg caagtaccag gatgaaaaga actatgaaat aaatgaagga    3000
agctacaagt gtgtgtgtat atgtatatgt atatatctct atatttacat atatatatta    3060
aaattgcatg gacagagac tttgcaatcc gaaagaatag actgtgaaat gagttcttaa     3120
agaaaagact tgtttatgta ttaaaaaaac cacttcacag tgagtcgctt tggcttttg     3180 ataaactgcg gcctgctctc agggtggggt gactattttt gaattcctat ttattttttg    3240
tgtttgtccc tgattttttt tttttaattc tatggcttcc tatctggcag cttaatgggt    3300 aattttgag gtatgtattt aacaaaataa acgacactgc cgaaaaaaaa aaagtgaag      3360 tgaaaacaat cagggcacat taaaatgata caagtcaaat aaatcttaaa gacacaatgc    3420
acacttaaaa tgactcaata aaatgacttg ctacgttccg ttattcaatt tgtcattact    3480
gtagtgaaca gatgcatttc tgtggaattc caaataagta aaactgaaat tcagtgcaga    3540
gaaaactttg tccactagtg caagtcttga tcaaatgaca ttttgacatt ggacatatgg    3600
aattcatagt atgagccaca ttttgttgtg aaatttattt acctgcttgt ggcttcaaat    3660
ctgaaaatta ataagcctgc tcgtttaaaa gttgtttgtt gttgctgttt tttttgtcttt   3720 ttgtttttta ctagaaaata gttcagtgta atattaagtt agaaagaag ttgctgccca     3780 gttaaagggg ctccctctca aataaatctc catccttccc tctcccaaaa gacatttctg    3840
atttctgctt cactttgggc ttcctcttct tcgtacacat tccatctacc taatcaaaca    3900
ttttcagtcc ctgatctctc ctgtcccttt tcctgggatg acagccctaa caagaactgt    3960
ttttgaatcg ttgtgcagct ccaggcaata gagtatgtga agcgatttca gtagaatcac    4020
ttactcatcc taaaagaaaa cattatccca gttacctaca tcgcaattac cttatgtaaa    4080
gcagaactaa tgctgactgg atgtttaatg ggatgagcat taaagctgca atctactata    4140
gtactccaga tctctttcgg cttcctatga gaaacaccag aagcattact ttccacttct    4200
acttacagta attgcaagag gagacctcac attcaggact ggcctagtga acgtaatcca    4260
tgctttaaac tggccattaa acagtcccac atggttggat ttttttttttt ttttttgagtt  4320 gtgctttcac aaaaccttgt caaagacctc atgcaatatc actttgaaag ttattttctg    4380
tttactacac aaacattgta atataactgt taatactatt tatatatttg aaaggtataa    4440
aaggtaggag ttaaaaaaaa aacctctatg tgtagatatt aactcagaac ttacaatata    4500
cagggagaag acatgttgca atacaagcta attctagctg ctcagtaacc tctggagttt    4560
ttaaagggac attttcctgt actttttcaa ataatgatgt ttaaaaatta tcttgacata    4620
agcgtcatat acctttgcaa aaggatggtt gtttgcagtt agccctggcc ccatccttcc    4680
tatttctgta gtatgctgca gctttaatca gaaagtccat ggttgctgct tcctgatctc    4740
cgagttactc tttccaaatt gtcttcttac actgttgctg aaggtcactc tgtacacgta    4800
```

```
atggaaactg attttgccaa gctcttacaa ggtggttcat ctatcgatgg catccgcatt    4860
tggtatcttt tacacttcaa ccaaaaattt attaggtatt tttcaatgct aagtcttgcc    4920
ttttattttt taatttcact gccaagtttg cagtggttct aagtgaatct gtgggcattt    4980
tagcctgtgg tcttgccaga tctttgcgaa ttacaatgca tatatgtcta tttattcaat    5040
atctgtcata taatatctat ttggaagaag aaactttctc ttgtagtgcc tcttgacaaa    5100
gcacaatttc ccgccttttt ttttttttgt gaaatgaaaa aaacaaattg tgttttattg    5160
cggtatcaac aatgtgaata aggattaaca tattgtaaat gttcttttt  ccatgtaaat    5220 caactatctt tgttatcact aagtgataat taatttttaa cttatgtgca ttgttaggct    5280
gttagaattt tttggttgtt aaaataaacg cattcaat                            5318
```

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
gtgtcccaag ctgtctttg                                                 19

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
cttggccctt ttcatctcc                                                 19

USE OF PROTEIN SATB2 AS A MARKER FOR COLORECTAL CANCER

This application is a Continuation of U.S. application Ser. No. 12/302,248 filed Feb. 17, 2009, U.S. Pat. No. 8,067,190 which is the National Phase of PCT/EP2007/004931 filed on Jun. 4, 2007, which claims priority under 35 U.S.C. 119(e) to U.S. Provisional Application No. 60/816,613 filed on Jun. 27, 2006 and under 35 U.S.C. 119(a) to Patent Application No. EP 06114954.8 filed in Europe on Jun. 2, 2006. The entire content of each of the above-identified applications is hereby incorporated by reference.

FIELD OF THE INVENTION

The present invention relates to the field of cancer diagnostics and prognosis. In particular, it provides a new means for use in detection and characterization of colo-rectal cancer, via the identification of the SATB2 protein as a marker for this cancer type.

BACKGROUND OF THE INVENTION

SATB2

The gene encoding special AT-rich sequence-binding protein 2 (SATB2) was identified in 1999 during the massive effort of sequencing the human genome (Kikuno R et al (1999) DNA Res. 6:197-205). Since then, the SATB2 gene has been considered as expressed mainly in neuronal tissue.

SATB2 is a transcription factor that form parts of the nuclear matrix and orchestrates gene expression in a tissue-specific manner by regulating high-order chromatin structure through interaction with AT-rich sequences, also referred to as matrix attachment regions (MARs) (Dickinson L A et al (1992) Cell 70, 631-45; FitzPatrick D R et al (2003) Hum. Mol. Genet. 12, 2491-501; Yasui D, (2002) Nature 419, 641-5; Bode, J (2000) Crit. Rev. Eukaryot. Gene. Expr. 10, 73-90).

Studies of the gene and its protein product, the SATB2 protein, point towards an involvement in regulation of gene expression as a transcription factor in neuronal tissue (Dobreva G et al (2003) Genes Dev. 17:3048-3061; Britanova O et al (2005) Eur. J. Neurosci. 21:658-668). The SATB2 gene has also been described to have a role in palate development and cleft palate (FitzPatrick D R et al (2003) Human Mol. Genet. 12:2491-2501; van Buggenhout G et al (2005) Eur. J. Med. Genet. 48:276-289).

Salahshor et al studied a patient with the adenomatous polyopsis coli (APC) gene mutation (Salahshor et al (2005) BMC cancer 5:66). APC patients develop an abnormal amount of colonic adenomas at a young age that eventually, if left untreated, will progress to colo-rectal cancer. Global gene expression profiling revealed that a group of 84 genes, including SATB2, had a significantly altered expression in adenomas compared to normal mucosa. SATB2 was found significantly down-regulated but was not selected for any further analysis. A recent expression profiling study of colo-rectal cancer in Int J Cancer likewise indicated an altered expression status for SATB2 at the mRNA level (Groene J et al (2006) Int J Cancer 119, 1829-1836).

PCT publications WO03/022126 and WO2006/015742 describe other, similar studies directed to expression profiling of cancer cells. The expression of a multitude of genes, including SATB2, is analyzed and conclusions are drawn from the overall expression patterns.

Importantly, the studies referred to above provide no suggestions concerning the use of the SATB2 protein as a specific colo-rectal marker or the use of SATB2 as a prognostic tool for colo-rectal cancer.

Cancer

Cancer is one of the most common causes of disease and death in the western world. In general, incidence rates increase with age for most forms of cancer. As human populations continue to live longer, due to an increase of the general health status, cancer will affect an increasing number of individuals. The cause of most common cancer types is still at large unknown, although there is an increasing body of knowledge providing a link between environmental factors (dietary, tobacco smoke, UV radiation etc) as well as genetic factors (germ line mutations in "cancer genes" such as p53, APC, BRCA1, XP etc) and the risk for development of cancer.

No definition of cancer is entirely satisfactory from a cell biological point of view, despite the fact that cancer is essentially a cellular disease and defined as a transformed cell population with net cell growth and anti-social behavior. Malignant transformation represents the transition to a malignant phenotype based on irreversible genetic alterations. Although this has not been formally proven, malignant transformation is believed to take place in one cell, from which a subsequently developed tumor originates (the "clonality of cancer" dogma). Carcinogenesis is the process by which cancer is generated and is generally accepted to include multiple events which ultimately lead to growth of a malignant tumor. This multi-step process includes several rate-limiting steps, such as addition of mutations and possibly also epigenetic events, leading to formation of cancer following stages of precancerous proliferation. The most common forms of cancer arise in somatic cells and are predominantly of epithelial origin (skin, prostate, breast, colon and lung) followed by cancers originating from the hematopoetic lineage (leukemia and lymphoma) and mesenchymal cells (sarcomas). The stepwise changes involve accumulation of errors (mutations) in vital regulatory pathways that determine cell division, asocial behavior and cell death. Each of these changes provides a selective Darwinian growth advantage compared to surrounding cells, resulting in a net growth of the tumor cell population. It is important to emphasize that a malignant tumor does not only consist of the transformed tumor cells themselves but also surrounding normal cells which act as a supportive stroma. This recruited cancer stroma consists of connective tissue, blood vessels and various other normal cells, e.g. inflammatory cells, which act in concert to supply the transformed tumor cells with signals necessary for continued tumor growth.

Cancer Diagnostics

Microscopic evaluation of a tissue section taken from a tumor remains the golden standard for determining a diagnosis of cancer. Analysis of genomic DNA, transcribed genes and expressed proteins all add important information to the histological features detected in the microscope. Tomorrow's diagnosis, prognostic information and choice of treatment will in all likelihood be based on a synoptic evaluation of morphology in conjunction with analyses of nucleic acids and proteins. Already today, evolving knowledge based on the human genome sequence and biochemical pathways, including signaling inside and between cells in a tissue, enable the dissection of some of the mechanisms that underlie different stages in tumor formation as well as variation of phenotypes, which define the different types of cancer.

Despite remarkable progress within molecular biology, cancer diagnostics still relies on the use of light microscopy. The development of molecular tools has played an important, although as of yet incremental, role to discriminate a cancer cell from a normal cell. The most commonly used method in addition to histochemical staining of tissue sections is immunohistochemistry. Immunohistochemistry allows the detection of protein expression patterns in tissues and cells using specific antibodies. The use of immunohistochemistry in clinical diagnostics has provided a possibility to not only analyze tissue architecture and cellular morphology, but also to detect immunoreactivity in different cell populations. This has been important to support accurate grading and classification of different primary tumors as well as in the diagnostics of metastases of unknown origin. The most commonly used antibodies in clinical practice today include antibodies against cell type markers, e.g. PSA, MelanA, Thyroglobulin and antibodies recognizing intermediate filaments, cluster of differentiation (CD) antigens etc. and markers of malignant potential, e.g. Ki67, p53, HER-2. Aside from immunohistochemistry, the use of in situ hybridization for detecting gene amplification and gene sequencing for mutation analysis are evolving technologies within cancer diagnostics.

Colo-Rectal Cancer

Colo-rectal cancer is one of the most common forms of human cancer worldwide. Data from the GLOBOCAM 2002 database presented by Parkin et al show that around 1 million new cases of colo-rectal cancer are found yearly (Parkin et al (2007) CA Cancer J Clin 55, 74-108). Further, the incidence of colo-rectal cancer in the world is approximately 9.4% of all cancers, and colo-rectal cancer constitutes the second most common cause of death in the western world. The five-year survival rate of colo-rectal cancer is approximately 60% in the western world but as low as 30% in Eastern Europe and India.

Early detection and surgery with excision of the tumor is currently of critical importance for a favorable prognosis. Symptoms depend on where in the distal gastro-intestinal tract the tumor is located, and include bowel distress, diarrhea, constipation, pain and anemia (secondary to bleeding from the tumor into the bowel). Malignant tumors may be categorized into several stages according to different classification schemes, such as the TNM/UICC classification I-IV or Dukes' stages A-C. The least malignant tumors (Dukes' stages A and B) have a reasonably favorable outcome, while on the other end some highly malignant tumors with metastasis (Dukes' stage C) have poor survival rates. Current diagnostics are based on patient history, clinical and endoscopic examination (rectoscopy and colonoscopy) optionally followed by radiological mapping to determine extensiveness of tumor growth. In conjunction with endoscopic examination, tissue biopsies are performed from dubious lesions.

For microscopic diagnosis, biopsy material from suspected tumors is collected and examined under a microscope. To obtain a firm diagnosis, the tumor tissue is then fixated in formalin, histo-processed and paraffin embedded. From the resulting paraffin block, tissue sections can be produced and stained using both histochemical and immunohistochemical methods.

For localized tumors, i.e. tumors that have not evolved into a metastasizing disease, surgical intervention with radical resection of the tumor and surrounding bowel and tissues is performed. The surgical specimen is then sent to pathology for gross and microscopical analysis. This analysis forms the basis for staging of the tumor. The by far most common form of colo-rectal cancer is adenocarcinoma, representing a tumor of glandular origin, which can be highly, moderately or lowly differentiated.

For primary tumors, hematoxylin-eosin stained tissue sections are sufficient to enable a correct diagnosis and classification according to the different colo-rectal cancer classifications. However, as colo-rectal cancer is very common and has often grown to a considerable size before detection, metastases are not uncommon. The tumor typically metastasizes to regional lymph nodes, but distant metastasis in the liver and lung is not unusual. A common clinical problem with cancer is patients that present a metastasis of unknown origin. In the case where a metastasis is an adenocarcinoma, several possible primary tumors can be suspected, e.g. breast, prostate, pancreatic, stomach and colo-rectal cancer. For differential diagnostics, immunohistochemical markers can be used that recognize features inherent in the cell of origin. At present, cytokeratin 20 (CK20), an intermediate filament marker abundant in the glandular cells of the GI-tract, is used to characterize colo-rectal cancer. However, several other adenocarcinomas can also be positive for CK20 antibodies, whereas not all colo-rectal cancers are positive. Furthermore, there are no markers available today that can distinguish tumors of low malignancy grade and low risk for metastasis from highly malignant tumors with a reduced chance of survival.

In order for doctors to give specific treatment for the right type of cancer and as early as possible, the provision of new molecular markers that are specific to colo-rectal cancer alone, and affords the possibility of differentiating patients into different risk categories is crucial. In summary, there is a great demand for new means to advance the diagnostics and screening of colo-rectal cancer.

DISCLOSURE OF THE INVENTION

It is an object of the present invention to meet this demand through the provision of a marker useful for the diagnosis and/or prognosis of colo-rectal cancer in a subject.

It is a related object of the invention to provide a marker which is useful for distinguishing between colo-rectal cancers and other types of cancer.

It is another object of the present invention to provide new methods for the diagnosis, prognosis and/or treatment of colo-rectal cancer.

It is a related object of the present invention to provide a kit that can be used in connection with methods for the diagnosis, prognosis and/or treatment of colo-rectal cancer.

Another object of the present invention is to provide novel compounds useful for diagnosis, prognosis and/or therapy of colo-rectal cancer.

For these and other objects apparent to the skilled person from the present disclosure, the present invention provides, in its different aspects, new means for determining the status and prognosis of colo-rectal cancer, and for the treatment thereof.

Thus, in a first aspect, the present invention provides a method for determining whether a prognosis for colo-rectal cancer in a mammalian subject having or suspected of having colo-rectal cancer is poor, comprising the steps of:

a) providing a sample from the subject;

b) quantifying the amount of SATB2 protein present in said sample to yield a sample value;

c) comparing the sample value obtained in step b) with a reference value; and, if said sample value is lower than said reference value, d) concluding that the prognosis for colo-rectal cancer in said subject is poor.

This first aspect of the present invention is based on the previously unrecognized fact that the expression of SATB2 protein in samples from a subject having or suspected of having colo-rectal cancer may serve as an indicator of disease status in subjects. More particularly, the present invention identifies for the first time a correlation between a low value of SATB2 expression on the one hand and more aggressive or high-risk forms of colo-rectal cancer on the other. The present invention based on SATB2 expression as an indicator of colo-rectal cancer prognosis has a number of benefits. For cancer in general, early detection of aggressive forms is of vital importance as it enables curing treatment. This is particularly true for colo-rectal cancer, for which several large studies have shown that subjects with early cancers, i.e. representing stage 1 and stage 2 tumors (essentially Dukes' A and B), have a substantially better prognosis as compared to subjects with late stage tumors. This difference is not dependent on the mode of treatment since radical resection is performed for all types of colo-rectal cancer. Rather, the large difference in survival is clearly related to early detection, correct diagnosis and adequate surgical treatment. The SATB2 protein, as a marker for which a certain level of expression is correlated with a certain pattern of disease progression, has a great potential for example in a panel for differential diagnostics of metastasis.

In an embodiment of the invention, the conclusion in step d) of a poor prognosis may involve establishing that said subject has a shorter expected survival time than would have been the case if the subject had not exhibited a low SATB2 expression value. Alternatively or also, the conclusion of a poor prognosis may involve establishing a lower likelihood of five-year survival than would have been the case if the subject had not exhibited a low SATB2 expression value. For example, the conclusion may be that said subject has a likelihood of five-year survival of 65% or lower, for example 60% or lower, 50% or lower, 40% or lower or 30% or lower.

Further, regarding subjects having or suspected of having node negative tumors, the conclusion may be that said subject has a likelihood of five-year survival of 73% or lower, for example 70% or lower, for example 60% or lower, 50% or lower, 40% or lower or 30% or lower. Regarding female subjects, the conclusion may be that said subject has a likelihood of five-year survival of 74% or lower, for example 70% or lower, for example 60% or lower, 50% or lower, 40% or lower or 30% or lower. Regarding female patients having or suspected of having node negative tumors, the conclusion may be that said subject has a likelihood of five-year survival of 80% or lower, for example 75% or lower, for example 70% or lower, for example 60% or lower, 50% or lower, 40% or lower or 30% or lower.

The identified correlation between low SATB2 expression and high-risk forms of colo-rectal cancer may also form the basis for a decision to apply a different regime for treatment of the subject than would have been the case if the subject had not exhibited a low SATB2 expression value. Thus, in a second aspect, the present invention provides a method of treatment of colo-rectal cancer in a subject in need thereof, comprising a) providing a sample from the subject;
b) quantifying the amount of SATB2 protein present in said sample to yield a sample value;
c) comparing the sample value obtained in step b) with a reference value; and, if said sample value is lower than said reference value,
d) treating said subject with a treatment regimen adapted to a poor prognosis of colo-rectal cancer In one embodiment of the invention, the treatment regimen is selected from chemotherapy, neo-adjuvant therapy and combinations thereof.

Thus, the treatment regimen may be neo-adjuvant therapy. Such neo-adjuvant therapy may consist of radiation therapy only or of radiation therapy in combination with chemotherapy.

In the method aspects of the present invention described above, the subject may have, or be suspected of having, colo-rectal cancer in different forms and/or stages.

In some embodiments of these aspects, the colo-rectal cancer in question is a node-negative colo-rectal cancer, i.e. colo-rectal cancer that has not progressed to the lymph node metastazing stage. In other similar embodiments, the colo-rectal cancer in question is characterized as being in either Dukes' stage A or B. In yet other embodiments, the colo-rectal cancer in question is colo-rectal adenoma or colo-rectal carcinoma. In these embodiments, determining that the subject exhibits low SATB2 expression may be of great value for the prognosis of future progression of the disease and thus form the basis for an informed decision with regard to future disease management. Within a group of subjects afflicted with such a comparatively early stage of disease, subjects with low SATB2 expression likely are at a comparatively high risk of developing a more aggressive disease. Low SATB2 expression among subjects having node-negative colo-rectal cancer or Dukes' stage A or B colo-rectal cancer may therefore indicate that these subjects should be monitored more closely and/or treated differently than subjects that do not exhibit low SATB2 expression. The methods according to the invention therefore offers the possibility of a greater chance for survival over a certain period of time and/or longer survival time for such subjects, owing to the additional prognostic information given by the SATB2 marker.

In other embodiments, the colo-rectal cancer in question is metastazing colo-rectal cancer. In other similar embodiments, the colo-rectal cancer in question is characterized as being in Dukes' stage C.

In embodiments of the invention, the subject is a human, such as a woman. As shown in the appended examples, the prognostic value of the SATB2 marker is especially marked in the group of human, female subjects having node-negative forms of colo-rectal cancer.

A determination that the sample value of SATB2 protein expression is lower than the reference value is sometimes referred to herein as a determination of "low SATB2 expression".

In the methods of the invention, the reference value for use as comparison with the sample value for a subject may be established in various ways. As one non-limiting example, the reference value may correspond to the amount of SATB2 expression in healthy tissue of the subject undergoing the prognosis or therapy. As another example, the reference value may be provided by the amount of SATB2 expression measured in a standard sample of normal tissue from another, comparable subject. As another example, the reference value may be provided by the amount of SATB2 expression measured in a standard sample of tumor tissue, such as tissue from a Dukes' stage A or B cancer.

The reference value may be obtained in the course of carrying out the method according to the above aspects of the present invention. Alternatively, the reference value is a predetermined value obtained from a reference sample and corresponding to the amount of SATB2 expression in said reference sample.

One alternative for the quantification of SATB2 expression in a sample is the determination of the fraction of cells in the sample exhibit SATB2 expression over a certain level. This determination may for example be performed as described below in the Examples, section 4, definition of "fraction score". In embodiments of the methods of the above aspects of the present invention, the criterion for the conclusion in step d) is a sample value for the nuclear fraction of SATB2 positive cells, i.e. a "fraction score", which is lower than the reference value of 50%, such as lower than 40%, such as lower than 30%, such as lower than 25%, such as lower than 20%, such as lower than 15%, such as lower than 10%, such as lower than 5%, such as lower than 1%. Further, the determination of a poor prognosis may correspond to a detection of essentially no SATB2 positive cells in a sample, i.e. a "fraction score" of essentially zero.

Another alternative for the quantification of SATB2 expression in a sample is the automated measurement of an autoscore for SATB2 expression using an automated scanner and image processing software. This determination may for example be performed as described below in the Examples, section 5, definition of "autoscore". In embodiments of the methods of the above aspects of the present invention, the criterion for the conclusion in step d) is a sample value for the expression of SATB2 in the sample cells, i.e. an "autoscore", which is lower than the reference value of 70, such as lower than 60, such as lower than 50, such as lower than 40, such as lower than 30, such as lower than 25, such as lower than 20, such as lower than 15, such as lower than 10, such as lower than 5.

In some embodiments of the invention, the measurement of sample value and/or reference value, whether as a fraction score or autoscore as above or as some other known or adapted variable, is performed on glandular cells from the distal gastro-intestinal tract from a subject, i.e. appendix, colon and/or rectum, and/or on colo-rectal cancer cells.

In another embodiment of the invention, a determination of poor prognosis corresponds to no detectable SATB2 expression in glandular cells from the distal gastro-intestinal tract from a subject.

In the context of the present invention, the terms "sample value" and "reference value" are to be interpreted broadly. As described above, the quantification of SATB2 expression to obtain these values may be done via automatic means, or via a scoring system based on visual or microscopic inspection of samples. However, it is also possible for a skilled person, such as a person skilled in the art of histopathology, to determine the sample and reference values merely by inspection of e.g. tissue slides that have been stained for SATB2 expression. The determination of the sample value being lower than the reference value may thus correspond to the determination, upon visual or microscopic inspection, that a sample tissue slide is less densely stained and/or exhibit fewer stained cells than is the case for a reference tissue slide. In this case, the sample and reference values are thought of as mental values that the skilled person determines upon inspection and comparison. Thus, the invention is not limited to the use of automatic analysis.

The particular procedure used for detection of the expression of SATB2 protein in the methods of the present invention is not limited in any particular way. In some embodiments of the methods according to the invention, step b) comprises:

b1) applying to the sample a quantifiable affinity ligand capable of selective interaction with the SATB2 protein to be quantified, said application being performed under conditions that enable binding of the affinity ligand to any SATB2 protein present in the sample;

b2) removing non-bound affinity ligand; and b3) quantifying any affinity ligand remaining in association with the sample.

In such embodiments, the sample from the subject may be a body fluid sample, such as a sample of blood, plasma, serum, cerebral fluid, urine, semen and exudate. In the method according to the invention, the sample may, alternatively, be a stool sample, a cytology sample or a tissue sample, such as a sample of colo-rectal tissue.

In a preferred embodiment, the method according to the invention is carried out in vitro.

The skilled person will recognize that the usefulness of the present invention is not limited to the quantification of any particular variant of the SATB2 protein present in the subject in question, as long as the protein is encoded by the relevant gene and presents the relevant pattern of expression. As a non-limiting example, the SATB2 protein has an amino acid sequence which comprises a sequence selected from:

i) SEQ ID NO:1; and ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

As another non-limiting example, the SATB2 protein has an amino acid sequence which comprises a sequence selected from:

i) SEQ ID NO:2; and ii) a sequence which is at least 85% identical to SEQ ID NO:2.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2.

In embodiments of the methods according to the invention, the SATB2 protein is detected and/or quantified through the application to a sample of a detectable and/or quantifiable affinity ligand, which is capable of specific or selective interaction with the SATB2 protein. The application of the affinity ligand is performed under conditions that enable binding of the affinity ligand to any SATB2 protein in the sample. It is regarded as within the capabilities of those of ordinary skill in the art to select or manufacture the proper affinity ligand and to select the proper format and conditions for detection and/or quantification, once the connection between SATB2 and colo-rectal cancer is known through the teaching of the present disclosure. Nevertheless, examples of affinity ligands that may prove useful, as well as examples of formats and conditions for detection and/or quantification, are given below for the sake of illustration.

Thus, in some embodiments of the invention, an affinity ligand is used, which is selected from the group consisting of antibodies, fragments thereof and derivatives thereof, i.e. affinity ligands based on an immunoglobulin scaffold. Antibodies comprise monoclonal and polyclonal antibodies of any origin, including murine, human and other antibodies, as well as chimeric antibodies comprising sequences from different species, such as partly humanized mouse antibodies. Polyclonal antibodies are produced by immunization of animals with the antigen of choice, whereas monoclonal antibodies of defined specificity can be produced using the hybridoma technology developed by Köhler and Milstein (Köhler G and Milstein C (1976) Eur. J. Immunol. 6:511-519). Antibody fragments and derivatives comprise Fab fragments, consisting of the first constant domain of the heavy chain (CH1), the constant domain of the light chain (CL), the variable domain of the heavy chain (VH) and the variable domain of the light chain (VL) of an intact immunoglobulin protein; Fv fragments, consisting of the two variable antibody domains VH and VL (Skerra A and Pluckthun A (1988) Science 240: 1038-1041); single chain Fv fragments (scFv), consisting of the two VH and VL domains linked together by a flexible peptide linker (Bird R E and Walker B W (1991) Trends Biotechnol. 9:132-137); Bence Jones dimers (Stevens F J et al (1991) Biochemistry 30:6803-6805); camelid heavy-chain dimers (Hamers-Casterman C et al (1993) Nature 363:446-448) and single variable domains (Cai X and Garen A (1996) Proc. Natl. Acad. Sci. U.S.A. 93:6280-6285; Masat L et al (1994) Proc. Natl. Acad. Sci. U.S.A. 91:893-896), and single domain scaffolds like e.g. the New Antigen Receptor (NAR) from the nurse shark (Dooley H et al (2003) Mol. Immunol. 40:25-33) and minibodies based on a variable heavy domain (Skerra A and Pluckthun A (1988) Science 240:1038-1041).

Polyclonal and monoclonal antibodies, as well as their fragments and derivatives, represent the traditional choice of affinity ligands in applications requiring selective biomolecular recognition, such as in the detection and/or quantification of SATB2 protein according to the invention. However, those of skill in the art know that, due to the increasing demand of high throughput generation of specific binding ligands and low cost production systems, new biomolecular diversity technologies have been developed during the last decade. This has enabled a generation of novel types of affinity ligands of both immunoglobulin as well as non-immunoglobulin origin that have proven equally useful as binding ligands in biomolecular recognition applications and can be used instead of, or together with, immunoglobulins.

The biomolecular diversity needed for selection of affinity ligands may be generated by combinatorial engineering of one of a plurality of possible scaffold molecules, and specific and/or selective affinity ligands are then selected using a suitable selection platform. The scaffold molecule may be of immunoglobulin protein origin (Bradbury A R and Marks J D (2004) J. Immunol. Meths. 290:29-49), of non-immunoglobulin protein origin (Nygren P A and Skerra A (2004) J. Immunol. Meths. 290:3-28), or of an oligonucleotide origin (Gold L et al (1995) Annu. Rev. Biochem. 64:763-797).

A large number of non-immunoglobulin protein scaffolds have been used as supporting structures in development of novel binding proteins. Non-limiting examples of such structures, useful for generating affinity ligands against SATB2 for use in the present invention, are staphylococcal protein A and domains thereof and derivatives of these domains, such as protein Z (Nord K et al (1997) Nat. Biotechnol. 15:772-777); lipocalins (Beste G et al (1999) Proc. Natl. Acad. Sci. U.S.A. 96:1898-1903); ankyrin repeat domains (Binz H K et al (2003) J. Mol. Biol. 332:489-503); cellulose binding domains (CBD) (Smith G P et al (1998) J. Mol. Biol. 277:317-332; Lehtiö J et al (2000) Proteins 41:316-322); γ crystallines (Fiedler U and Rudolph R, WO01/04144); green fluorescent protein (GFP) (Peelle B et al (2001) Chem. Biol. 8:521-534); human cytotoxic T lymphocyte-associated antigen 4 (CTLA-4) (Hufton S E et al (2000) FEBS Lett. 475:225-231; Irving R A et al (2001) J. Immunol. Meth. 248:31-45); protease inhibitors, such as Knottin proteins (Wentzel A et al (2001) J. Bacteriol. 183:7273-7284; Baggio R et al (2002) J. Mol. Recognit. 15:126-134) and Kunitz domains (Roberts B L et al (1992) Gene 121:9-15; Dennis M S and Lazarus R A (1994) J. Biol. Chem. 269:22137-22144); PDZ domains (Schneider S et al (1999) Nat. Biotechnol. 17:170-175); peptide aptamers, such as thioredoxin (Lu Z et al (1995) Biotechnology 13:366-372; Klevenz B et al (2002) Cell. Mol. Life. Sci. 59:1993-1998); staphylococcal nuclease (Norman T C et al (1999) Science 285:591-595); tendamistats (McConell S J and Hoess R H (1995) J. Mol. Biol. 250:460-479; Li R et al (2003) Protein Eng. 16:65-72); trinectins based on the fibronectin type III domain (Koide A et al (1998) J. Mol. Biol. 284:1141-1151; Xu L et al (2002) Chem. Biol. 9:933-942); and zinc fingers (Bianchi E et al (1995) J. Mol. Biol. 247:154-160; Klug A (1999) J. Mol. Biol. 293:215-218; Segal D J et al (2003) Biochemistry 42:2137-2148).

The above mentioned examples of non-immunoglobulin protein scaffolds include scaffold proteins presenting a single randomized loop used for the generation of novel binding specificities, protein scaffolds with a rigid secondary structure where side chains protruding from the protein surface are randomized for the generation of novel binding specificities, and scaffolds exhibiting a non-contiguous hyper-variable loop region used for the generation of novel binding specificities.

In addition to non-immunoglobulin proteins, oligonucleotides may also be used as affinity ligands. Single stranded nucleic acids, called aptamers or decoys, fold into well-defined three-dimensional structures and bind to their target with high affinity and specificity. (Ellington A D and Szostak J W (1990) Nature 346:818-822; Brody E N and Gold L (2000) J. Biotechnol. 74:5-13; Mayer G and Jenne A (2004) BioDrugs 18:351-359). The oligonucleotide ligands can be either RNA or DNA and can bind to a wide range of target molecule classes.

For selection of the desired affinity ligand from a pool of variants of any of the scaffold structures mentioned above, a number of selection platforms are available for the isolation of a specific novel ligand against a target protein of choice. Selection platforms include, but are not limited to, phage display (Smith G P (1985) Science 228:1315-1317), ribosome display (Hanes J and Plückthun A (1997) Proc. Natl. Acad. Sci. U.S.A. 94:4937-4942), yeast two-hybrid system (Fields S and Song O (1989) Nature 340:245-246), mRNA display (Roberts R W and Szostak J W (1997) Proc. Natl. Acad. Sci. U.S.A. 94:12297-12302), SELEX (System Evolution of Ligands by Exponential Enrichment) (Tuerk C and Gold L (1990) Science 249:505-510) and protein fragment complementation assays (PCA) (Remy I and Michnick S W (1999) Proc. Natl. Acad. Sci. U.S.A. 96:5394-5399).

Thus, in embodiments of the invention, an affinity ligand may be used, which is a non-immunoglobulin affinity ligand derived from any of the protein scaffolds listed above, or an oligonucleotide molecule.

In some embodiments of the methods according to the invention, an affinity ligand capable of selective interaction with the SATB2 protein is detectable and/or quantifiable. The detection and/or quantification of such an affinity ligand may be accomplished in any way known to the skilled person for detection and/or quantification of binding reagents in assays based on biological interactions. Thus, any affinity ligand, as described in the previous section, may be used quantitatively or qualitatively to detect the presence of the SATB2 protein. These "primary" affinity ligands may be labeled themselves with various markers or are in turn detected by secondary, labeled affinity ligands to allow detection, visualization and/ or quantification. This can be accomplished using any one or more of a multitude of labels, which can be conjugated to the affinity ligand capable of interaction with SATB2 or to any secondary affinity ligand, using any one or more of a multitude of techniques known to the skilled person, and not as such involving any undue experimentation.

Non-limiting examples of labels that can be conjugated to primary and/or secondary affinity ligands include fluorescent dyes or metals (e.g. fluorescein, rhodamine, phycoerythrin, fluorescamine), chromophoric dyes (e.g. rhodopsin), chemiluminescent compounds (e.g. luminal, imidazole) and bioluminescent proteins (e.g. luciferin, luciferase), haptens (e.g. biotin). A variety of other useful fluorescers and chromophores are described in Stryer L (1968) Science 162:526-533 and Brand L and Gohlke J R (1972) Annu. Rev. Biochem.

41:843-868. Affinity ligands can also be labeled with enzymes (e.g. horseradish peroxidase, alkaline phosphatase, beta-lactamase), radioisotopes (e.g. $^3$H, $^{14}$C, $^{32}$P, $^{35}$S or $^{125}$I) and particles (e.g. gold). The different types of labels can be conjugated to an affinity ligand using various chemistries, e.g. the amine reaction or the thiol reaction. However, other reactive groups than amines and thiols can be used, e.g. aldehydes, carboxylic acids and glutamine.

The method aspects of the invention may be put to use in any of several known formats and set-ups, of which a non-limiting selection are discussed below.

In a set-up based on histology, the detection, localization and/or quantification of a labeled affinity ligand bound to its SATB2 target may involve visual techniques, such as light microscopy or immunofluoresence microscopy. Other methods may involve the detection via flow cytometry or luminometry.

As explained above, detection and/or quantification of SATB2 protein in a subject may be accomplished by removing a biological sample from the subject, such as a tissue sample (biopsy), for example from colo-rectal tissue, blood sample, cerebral fluid, urine or stool. The affinity ligand is applied to the biological sample for detection and/or quantification of the SATB2 marker protein. This procedure enables not only detection of SATB2 protein, but may in addition show the distribution and relative level of expression thereof.

The method of visualization of labels on the affinity ligand may include, but is not restricted to, fluorometric, luminometric and/or enzymatic techniques. Fluorescence is detected and/or quantified by exposing fluorescent labels to light of a specific wavelength and thereafter detecting and/or quantifying the emitted light of a specific wavelength. The presence of a luminescently tagged affinity ligand may be detected and/or quantified by luminescence developed during a chemical reaction. Detection of an enzymatic reaction is due to a color shift in the sample arising from chemical reaction. Those of skill in the art are aware that a variety of different protocols can be modified in order for proper detection and/or quantification.

In the method according to the invention, a biological sample may be immobilized onto a solid phase support or carrier, such as nitrocellulose or any other solid support matrix capable of immobilizing any SATB2 protein present in the biological sample applied to it. Some well-known solid state support materials useful in the present invention include glass, carbohydrate (e.g. Sepharose), nylon, plastic, wool, polystyrene, polyethene, polypropylene, dextran, amylase, films, resins, cellulose, polyacrylamide, agarose, alumina, gabbros and magnetite. If the primary affinity ligand is not labeled in itself, the supporting matrix can thereafter be washed with various buffers known in the art and then exposed to a secondary labeled affinity ligand, washed once again with buffers to remove unbound affinity ligands, and thereafter selective affinity ligands can be detected and/or quantified with conventional methods. The binding properties for an affinity ligand will vary from one solid state support to the other, but those skilled in the art will be able to determine operative and optimal assay conditions for each determination by routine experimentation.

A method to detect and/or quantify the SATB2 protein as required by the present invention is by linking the affinity ligand to an enzyme that can then later be detected and/or quantified in an enzyme immunoassay (such as an EIA or ELISA). Such techniques are well established, and their realization does not present any undue difficulties to the skilled person. In such methods, the biological sample is brought into contact with a solid material or with a solid material conjugated to an affinity ligand against the SATB2 protein, which is then detected and/or quantified with an enzymatically labeled secondary affinity ligand. Following this, an appropriate substrate is brought to react in appropriate buffers with the enzymatic label to produce a chemical moiety, which for example is detected and/or quantified using a spectrophotometer, fluorometer, luminometer or by visual means.

As stated above, primary and any secondary affinity ligands can be labeled with radioisotopes to enable detection and/or quantification. Non-limiting examples of appropriate radiolabels in the current invention are $^3$H, $^{14}$C, $^{32}$P, $^{35}$S or $^{125}$I. The specific activity of the labeled affinity ligand is dependent upon the half-life of the radiolabel, isotopic purity, and how the label has been incorporated into the affinity ligand. Affinity ligands are preferably labeled using well known techniques (Wensel T G and Meares C F (1983) in: *Radioimmunoimaging and Radioimmunotherapy* (Burchiel S W and Rhodes B A eds.) Elsevier, New York, pp 185-196). A thus radiolabeled affinity ligand can be used to visualize SATB2 protein by detection of radioactivity in vivo or in vitro. Radionuclear scanning with e.g. gamma camera, magnetic resonance spectroscopy or emission tomography function for detection in vivo and in vitro, while gamma/beta counters, scintillation counters and radiographies are also used in vitro.

A further aspect of the present invention provides a kit for carrying out the methods according to the method aspects of the invention above, which kit comprises:

a) a quantifiable affinity ligand capable of selective interaction with an SATB2 protein; and b) reagents necessary for quantifying the amount of the affinity ligand.

The various components of the kit according to the invention are selected and specified as described above in connection with the method aspects of the present invention.

Thus, the kit according to the invention comprises an affinity ligand against SATB2, as well as other means that help to quantify the specific and/or selective affinity ligand after it has bound specifically and/or selectively to SATB2. For example, the kit of the present invention may contain a secondary affinity ligand for detecting and/or quantifying a complex formed by any SATB2 protein and the affinity ligand capable of selective interaction with an SATB2 protein. The kit of the present invention may also contain various auxiliary substances other than affinity ligands, to enable the kit to be used easily and efficiently. Examples of auxiliary substances include solvents for dissolving or reconstituting lyophilized protein components of the kit, wash buffers, substrates for measuring enzyme activity in cases where an enzyme is used as a label, and substances such as reaction arresters that are commonly used in immunoassay reagent kits.

The kit according to the invention may also advantageously comprise a reference sample for provision of the reference value to be used for comparison with the sample value. Such a reference sample may for example be constituted by a sample of tissue having a predetermined amount of SATB2 protein, which may then be used by the person of skill in the art of pathology to determine the SATB2 expression status in the sample being studied, by ocular or automated comparison of expression levels in the reference sample and the subject sample.

As a further aspect of the present invention, there is provided the use of an SATB2 protein as a prognostic marker. Also provided is the use of an SATB2 protein as a prognostic marker for colo-rectal cancer.

As a related aspect of the invention, there is provided the use of an SATB2 protein, or an antigenically active fragment thereof, in the manufacture of a prognostic agent for the prognosis of colo-rectal cancer. An antigenically active fragment of an SATB2 protein is a fragment of sufficient size to be useful for the generation of an affinity ligand, e.g. an antibody, which will interact with an SATB2 protein comprising the fragment.

In embodiments of these use aspects of the invention, the SATB2 protein may, as a non-limiting example, have an amino acid sequence which comprises a sequence selected from:
i) SEQ ID NO:1; and
ii) a sequence which is at least 85% identical to SEQ ID NO:1.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:1.

As another non-limiting example, the SATB2 protein has an amino acid sequence which comprises a sequence selected from:
i) SEQ ID NO:2; and
ii) a sequence which is at least 85% identical to SEQ ID NO:2.

In some embodiments, sequence ii) above is at least 90% identical, at least 91% identical, at least 92% identical, at least 93% identical, at least 94% identical, at least 95% identical, at least 96% identical, at least 97% identical, at least 98% identical or at least 99% identical to SEQ ID NO:2.

As a further aspect thereof, the present invention provides an affinity ligand capable of selective interaction with an SATB2 protein, which is an antibody or a fragment or a derivative thereof. Such an antibody, or fragment or derivative thereof, may for example be one that is obtainable by a process comprising a step of immunizing an animal with a protein whose amino acid sequence comprises the sequence SEQ ID NO:1. Processes for the production of antibodies or fragments or derivatives thereof against a given target are known in the art, and may be applied in connection with this aspect of the present invention. Any of those variants of the SATB2 protein (SEQ ID NO:2) or the antigenically active fragment thereof (SEQ ID NO:1) that are discussed above may, of course, be used in such a process for generating an antibody or a fragment or derivative thereof.

As a further aspect thereof, the present invention provides use of the affinity ligand according to the invention as a prognostic agent. A preferred embodiment of this use is use of the affinity ligand as a prognostic agent for the prognosis of colo-rectal cancer. The present invention also provides use of the affinity ligand for the prognosis of colo-rectal cancer. As a related aspect thereof, the present invention provides use of the affinity ligand according to the invention in the manufacture of a prognostic agent for the prognosis of colo-rectal cancer.

The present invention also provides, in another aspect thereof, a method for the diagnosis of colo-rectal cancer, comprising a step of detecting an SATB2 protein. This aspect of the present invention is based on the finding that SATB2 can serve as a protein marker for colo-rectal tissue in general, and for colo-rectal cancer in particular. As detailed further below, antibodies generated towards a fragment of the SATB2 protein show a strong and selective nuclear immunoreactivity in glandular cells from the distal gastro-intestinal tract, i.e. the appendix, colon and rectum, and in colo-rectal cancer. The most striking finding is positivity in 11 out of 11 colo-rectal carcinomas. Aside from colo-rectal cancer, only very few other tumors were weak or moderately positive.

In addition, SATB2 is relatively little present in other types of cancer, which in turn makes affinity ligands directed against SATB2 highly interesting tools for specifically distinguishing colo-rectal cancer from other cancers. Most colo-rectal cancers are gland-derived and therefore classified as adenocarcinomas. This is a typical cancer type, and can derive from various other organs as well. Therefore, the finding of the present invention is highly interesting when used to type the tumor metastasis, where the organ origin of the tumor is often unknown. At present, the available molecular markers for colo-rectal cancer are cross-reactive with respect to other adenocarcinomas, and therefore it is difficult to locate a tumor and to identify the origin of a metastasis. The specific colo-rectal cancer marker according to the invention will enable a doctor to locate cancer efficiently, provide more efficient treatment, and eventually help give patients more dependable prognosis.

Another aspect of the present invention involves the simultaneous testing of cancer samples for the SATB2 and CK20 markers. As detailed in the Examples, section 6, the predictive value of the combination of testing for both SATB2 and CK20 expression in distinguishing colo-rectal cancer exceeds that of testing for each of the markers taken by themselves. Thus, the invention provides, in this aspect, a method of diagnosing colo-rectal cancer, comprising the steps of detecting the SATB2 protein and detecting the CK20 protein. Further, the invention provides a method for detecting if a metastasis is originating from a colo-rectal cancer by detecting the presence of the SATB2 protein and/or the CK20 protein. By combining the information from both CK20 and SATB2, patients would more easily obtain an accurate diagnosis for colo-rectal disease. The skilled person would be able to adapt the teachings herein relating to the detection of SATB2 to the method according to this aspect of the invention, and could perform the simultaneous or sequential detection and/or quantification of SATB2 and CK20 without undue burden in the light of the description herein and in the light of the knowledge in the field of for example immunohistochemistry.

An interesting aspect of the present invention is the predicted leakage of the SATB2 protein into plasma and stool in cancer patients. As a comparison, a well-known prostate cancer marker, PSA, which is also expressed in normal prostate, leaks from the prostate to plasma even in healthy patients. However, many prostate cancer patients have an elevated PSA level in their plasma, and therefore screening elevated levels of PSA in the blood is a common early screening procedure for men in the risk group for developing prostata cancer. It is predicted that the same is true also for the link between SATB2 and colo-rectal cancer. Thus, SATB2 is also useful as a tool for screening colo-rectal cancer by using human plasma or other body fluid or stool as the sample in the present invention. In this regard, the present invention corresponds to a valuable extension and possibly even replacement for the present colo-rectal cancer screens such as colo-rectoscopy or sigmoidoscopy, which are so uncomfortable that many people skip them, in spite of the fact that the American Cancer Institute recommends regular check-ups for colo-cancer risk groups. A screening method based on the present invention, using SATB2 as a marker protein for colo-rectal cancer, brings significant benefit for screening, early detection and treatment of patients that have been afflicted by this type of cancer.

In the context of the present invention, "prognosis" refers to the prediction of the course or outcome of a disease and its treatment. Prognosis may also refer to a determination of chance of survival or recovery from a disease, as well as to a prediction of the expected survival time of a subject. A prognosis may, specifically, involve establishing the likelihood for survival of a subject during a period of time into the future, such as three years, five years, ten years or any other period of time.

In the context of the present invention, "diagnosis" refers to the determination of the presence of, or the identification of, a disease or disorder. Diagnosis also refers to the conclusion reached through that process. In this context, "diagnostic" means relating to and aiding in the determination of the existence or nature of a disease. In the context of the present invention, "diagnosis" and "diagnostic" also mean monitoring any naturally occurring changes in a disease over time or any changes due to treatment.

As evident from the above definitions, the terms "prognosis" and "diagnosis" have overlapping meanings and are not mutually exclusive.

In the context of the present invention, "specific" or "selective" interaction of e.g. an affinity ligand with its target or antigen means that the interaction is such that a distinction between specific and non-specific, or between selective and non-selective, interaction becomes meaningful. The interaction between two proteins is sometimes measured by the dissociation constant. The dissociation constant describes the strength of binding (or affinity) between two molecules. Typically the dissociation constant between an antibody and its antigen is from $10^{-7}$ to $10^{-11}$ M. However, high specificity does not necessarily require high affinity. Molecules with low affinity (in the molar range) for its counterpart have been shown to be as specific as molecules with much higher affinity. In the case of the present invention, a specific or selective interaction refers to the extent to which a particular method can be used to determine the presence and/or amount of a specific protein, the target protein or a fragment thereof, under given conditions in the presence of other proteins in a sample of a naturally occurring or processed biological fluid. In other words, specificity or selectivity is the capacity to distinguish between related proteins. Specific and selective are sometimes used interchangeably in the present description.

In the context of the present invention, a "mono-specific antibody" is one of a population of polyclonal antibodies which has been affinity purified on its own antigen, thereby separating such mono-specific antibodies from other antiserum proteins and non-specific antibodies. This affinity purification results in antibodies that bind selectively to its antigen. In the case of the present invention, the polyclonal antisera are purified by a two-step immunoaffinity based protocol to obtain mono-specific antibodies selective for the target protein. Antibodies directed against generic affinity tags of antigen fragments are removed in a primary depletion step, using the immobilized tag protein as the capturing agent. Following the first depletion step, the serum is loaded on a second affinity column with the antigen as capturing agent, in order to enrich for antibodies specific for the antigen (see also Nilsson P et al (2005) Proteomics 5:4327-4337).

BRIEF DESCRIPTION OF THE FIGURES

FIG. 5A (left) shows a section with SATB2 expression, whereas FIG. 5B (right) shows a section wherein SATB2 expression is absent. Both tumor samples are shown in duplicate.

FIG. 8 shows a detailed comparison of CK20 and SATB2 expression based on immunohistochemical stainings of tissue from 122 subjects diagnosed with colo-rectal carcinomas. Tissue cores were scored for low or high SATB2 level and low or high CK20 level.

FIG. 9 shows a comparison of CK20 and SATB2 expression based on immunohistochemical stainings of lymph node metastases from 17 subjects diagnosed with colo-rectal carcinoma. Tissue cores were scored for SATB2 nuclear fraction and CK20 staining.

EXAMPLES

Figure 1:
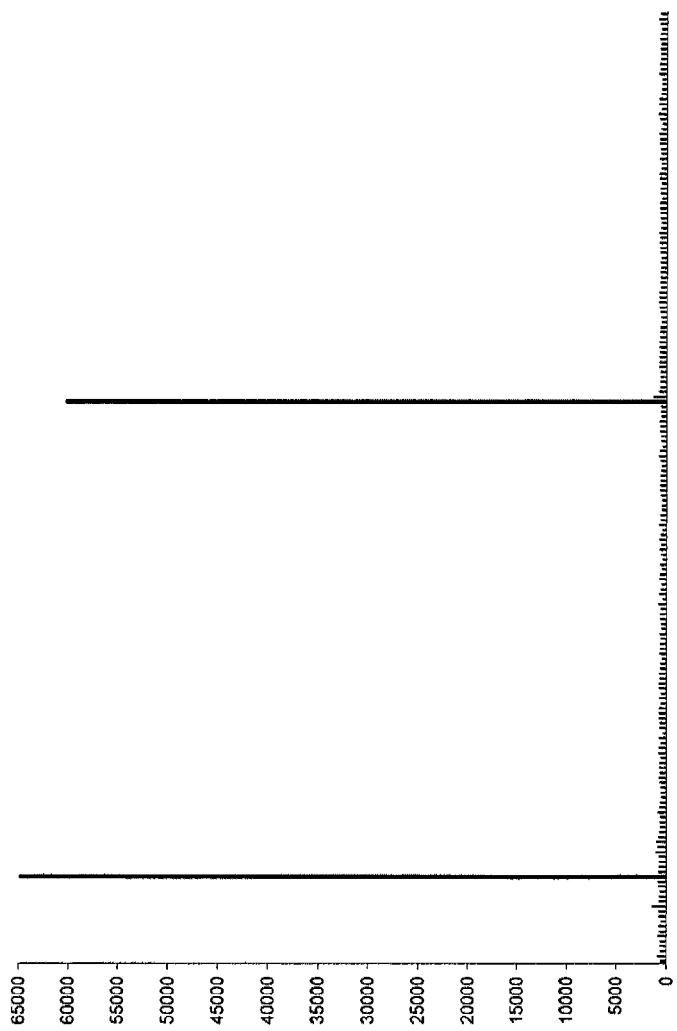
FIG. 1 illustrates the specificity of the antibody generated against an SATB2 fragment (SEQ ID NO:1) on a protein microchip containing an additional 94 different human proteins in duplicates.

Generation of Mono-Specific Antibodies Against SATB2 and Use thereof to Detect SATB2 in Normal and Cancerous Samples 1) Generation of Antigen
a. Materials and Methods A suitable fragment of the target protein encoded by the EnsEMBL Gene ID ENSG00000119042 was designed using bioinformatic tools with the human genome sequence as template (Lindskog M et al (2005) Biotechniques 38:723-727, EnsEMBL, www.ensembl.org). A fragment consisting of 123 amino acids corresponding to amino acids 377-499 (SEQ ID NO:1) of the protein SATB2 (SEQ ID NO:2; EnsEMBL entry no. ENSP00000260926) was designed. A polynucleotide encoding the target protein, which polynucleotide contained nucleotides 1542-1910 of the long SATB2 gene transcript (SEQ ID NO:3; EnsEMBL entry no. ENST00000260926), was isolated by a Superscript™ One-Step RT-PCR amplification kit with Platinum® Taq (Invitrogen) and a human total RNA pool panel as template (Human Total RNA Panel IV, BD Biosciences Clontech). Flanking restriction sites NotI and AscI were introduced into the fragment through the PCR amplification primers, to allow in-frame cloning into the expression vector (forward primer: GTGTCCCAAGCT-GTCTTTG (SEQ ID NO: 4), reverse primer: CTTGGC-CCTTTTCATCTCC (SEQ ID NO: 5)). Then, the downstream primer was biotinylated to allow solid-phase cloning as previously described, and the resulting biotinylated PCR product was immobilized onto Dynabeads M280 Streptavidin (Dynal Biotech) (Larsson M et al (2000) J. Biotechnol. 80:143-157). The fragment was released from the solid support by NotI-AscI digestion (New England Biolabs), ligated into the pAff8c vector (Larsson M et al, supra) in frame with a dual affinity tag consisting of a hexahistidyl tag for immobilized metal ion chromatography (IMAC) purification and an immunopotentiating albumin binding protein (ABP) from streptococcal protein G (Sjölander A et al (1997) J. Immunol. Methods 201:115-123; Stahl S et al (1999) Encyclopedia of Bioprocess Technology: Fermentation, Biocatalysis and Bioseparation (Fleckinger M C and Drew S W, eds) John Wiley and Sons Inc., New York, pp 49-63), and transformed into E. coli BL21(DE3) cells (Novagen). The sequences of the clones were verified by dye-terminator cycle sequencing of plasmid DNA amplified using TempliPhi DNA sequencing amplification kit (GE Healthcare, Uppsala, Sweden) according to the manufacturer's recommendations.

BL21(DE3) cells harboring the expression vector were inoculated in 100 ml 30 g/l tryptic soy broth (Merck KGaA) supplemented with 5 g/l yeast extract (Merck KGaA) and 50 mg/l kanamycin (Sigma-Aldrich) by addition of 1 ml of an overnight culture in the same culture medium. The cell culture was incubated in a 1 liter shake flask at 37° C. and 150 rpm until the optical density at 600 nm reached 0.5-1.5. Protein expression was then induced by addition of isopropyl-β-D-thiogalactopyranoside (Apollo Scientific) to a final concentration of 1 mM, and the incubation was continued overnight at 25° C. and 150 rpm. The cells were harvested by centrifugation at 2400 g, and the pellet was re-suspended in 5 ml lysis buffer (7 M guanidine hydrochloride, 47 mM $Na_2HPO_4$, 2.65 mM $NaH_2PO_4$, 10 mM Tris-HCl, 100 mM NaCl, 20 mM β-mercaptoethanol; pH=8.0) and incubated for 2 hours at 37° C. and 150 rpm. After centrifugation at 35300 g, the supernatant containing the denatured and solubilized gene products was collected.

The $His_6$-tagged fusion protein was purified by immobilized metal ion affinity chromatography (IMAC) on columns with 1 ml Talon® metal ($Co^{2+}$) affinity resin (BD Biosciences Clontech) using an automated protein purification procedure (Steen J et al (2006) Protein Expr. Purif. 46:173-178) on an ASPEC XL4™ (Gilson). The resin was equilibrated with 20 ml denaturing washing buffer (6 M guanidine hydrochloride, 46.6 mM $Na_2HPO_4$, 3.4 mM $NaH_2PO_4$, 300 mM NaCl, pH 8.0-8.2). The resin was then washed with a minimum of 31.5 ml washing buffer prior to elution in 2.5 ml elution buffer (6 M urea, 50 mM $NaH_2PO_4$, 100 mM NaCl, 30 mM acetic acid, 70 mM Na-acetate, pH 5.0). The eluted material was fractioned in three pools of 500, 700 and 1300 µl. The 700 µl fraction, containing the antigen, and the pooled 500 and 1300 µl fractions were stored for further use.

The antigen fraction was diluted to a final concentration of 1 M urea with phosphate buffered saline (PBS; 1.9 mM $NaH_2PO_4$, 8.1 mM $Na_2HPO_4$, 154 mM NaCl) followed by a concentration step to increase the protein concentration using Vivapore 10/20 ml concentrator with molecular weight cut off at 7500 Da (Vivascience AG). The protein concentration was determined using a bicinchoninic acid (BCA) micro assay protocol (Pierce) with a bovine serum albumin standard according to the manufacturer's recommendations. The protein quality was analyzed on a Bioanalyzer instrument using the Protein 50 or 200 assay (Agilent Technologies).

b) Results

A gene fragment corresponding to nucleotides 1542-1910 of the long transcript (SEQ ID NO:3) of the SATB2 gene and encoding a peptide (SEQ ID NO:1) consisting of amino acids 377 to 499 of the target protein SATB2 (SEQ ID NO:2) was successfully isolated by RT-PCR from a human RNA pool using primers specific for the protein fragment. However, there was one single silent nucleotide mutation in the sequence compared to the sequence of ENSG00000119042 from EnsEMBL. The 123 amino acid fragment (SEQ ID NO:1) of the target protein (SEQ ID NO:2) was designed to lack transmembrane regions to ensure efficient expression in E. coli, and to lack any signal peptide, since those are cleaved off in the mature protein. In addition, the protein fragment was designed to consist of a unique sequence with low homology with other human proteins, to minimize cross reactivity of generated affinity reagents, and to be of a suitable size to allow the formation of conformational epitopes and still allow efficient cloning and expression in bacterial systems.

A clone encoding the correct amino acid sequence was identified, and, upon expression in E. coli, a single protein of the correct size was produced and subsequently purified using immobilized metal ion chromatography. After dilution of the eluted sample to a final concentration of 1 M urea and concentration of the sample to 1 ml, the concentration of the protein fragment was determined to be 7.4 mg/ml and was 98% pure according to purity analysis.

2) Generation of Antibodies a) Materials and Methods

The purified SATB2 fragment as obtained above was used as antigen to immunize a rabbit in accordance with the national guidelines (Swedish permit no. A 84-02). The rabbit was immunized intramuscularly with 200 µg of antigen in Freund's complete adjuvant as the primary immunization, and boosted three times in four week intervals with 100 µg antigen in Freund's incomplete adjuvant.

Antiserum from the immunized animal was purified by a three-step immunoaffinity based protocol (Agaton C et al (2004) J. Chromatogr. A 1043:33-40; Nilsson P et al (2005) Proteomics 5:4327-4337). In the first step, 10 ml of total antiserum was buffered with 10×PBS to a final concentration of 1×PBS (1.9 mM $NaH_2PO_4$, 8.1 mM $Na_2HPO_4$, 154 mM NaCl), filtered using a 0.46 µm pore-size filter (Acrodisc®, Life Science) and applied to a an affinity column containing 5 ml N-hydroxysuccinimide-activated Sepharose™ 4 Fast Flow (GE Healthcare) coupled to the dual affinity tag protein $His_6$-ABP (a hexahistidyl tag and an albumin binding protein tag) expressed from the pAff8c vector and purified in the same way as described above for the antigen protein fragment. In the second step, the flow-through, depleted of antibodies against the dual affinity tag $His_6$-ABP, was loaded at a flow rate of 0.5 ml/min on a 1 ml Hi-Trap NHS-activated HP column (GE Healthcare) coupled to the SATB2 protein fragment used as antigen for immunization (SEQ ID NO:1). The $His_6$-ABP protein and the protein fragment antigen had been coupled to the NHS activated matrix as recommended by the manufacturer. Unbound material was washed away with 1×PBST (1×PBS, 0.1% Tween20, pH 7.25), and captured antibodies were eluted using a low pH glycine buffer (0.2 M glycine, 1 mM EGTA, pH 2.5). The eluted antibody fraction was collected automatically, and loaded onto two 5 ml HiTrap™ desalting columns (GE Healthcare) connected in series for efficient buffer exchange in the third step. The second and third purification steps were run on the AKTAxpress™ platform (GE Healthcare). The antigen selective (mono-specific) antibodies (msAbs) were eluted with PBS buffer, supplemented with glycerol and $NaN_3$ to final concentrations of 50% and 0.02%, respectively, for long term storage at −20° C. (Nilsson P et al (2005) Proteomics 5:4327-4337).

The specificity and selectivity of the affinity purified antibody fraction were analyzed by binding analysis against the antigen itself and against 94 other human protein fragments in a protein array set-up (Nilsson P et al (2005) Proteomics 5:4327-4337). The protein fragments were diluted to 40 µg/ml in 0.1 M urea and 1×PBS (pH 7.4) and 50 µl of each was transferred to the wells of a 96-well spotting plate. The protein fragments were spotted and immobilized onto epoxy slides (SuperEpoxy, TeleChem) using a pin-and-ring arrayer (Affymetrix 427). The slide was washed in 1×PBS (5 min) and the surface was then blocked (SuperBlock®, Pierce) for 30 minutes. An adhesive 16-well silicone mask (Schleicher & Schuell) was applied to the glass before the mono-specific antibodies were added (diluted 1:2000 in 1×PBST to appr. 50 ng/ml) and incubated on a shaker for 60 min. Affinity tag-specific IgY antibodies were co-incubated with the mono-specific antibodies in order to quantify the amount of protein in each spot. The slide was washed with 1×PBST and 1×PBS twice for 10 min each. Secondary antibodies (goat anti-rabbit antibody conjugated with Alexa 647 and goat anti-chicken antibody conjugated with Alexa 555, Molecular Probes) were diluted 1:60000 to 30 ng/ml in 1×PBST and incubated for 60 min. After the same washing procedure as for the first incubation, the slide was spinned dry and scanned (G2565BA array scanner, Agilent) and images were quantified using image analysis software (GenePix 5.1, Axon Instruments). The results are discussed below and presented in FIG. 1.

Figure 2:
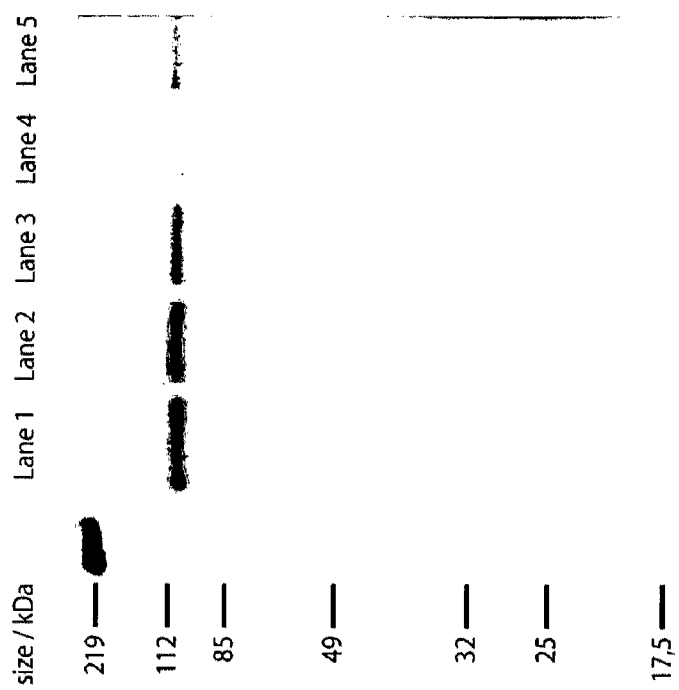
FIG. 2 shows a tissue Western blot analysis of the purified mono-specific antibody. Total protein extracts from human cell lines RT-4 (lane 1), EFO-21 (lane 2) and A-431 (lane 3), as well as from normal human liver (lane 4) and normal human tonsil (lane 5).

In addition, the specificity and selectivity of the affinity purified antibody were analyzed by Western blot. Western blot was performed by separation of total protein extracts from selected human cell lines and tissues on pre-cast 10-20% Criterion™ SDS-PAGE gradient gels (Bio-Rad Laboratories) under reducing conditions, followed by electro-transfer to PVDF membranes (Bio-Rad Laboratories) according to the manufacturer's recommendations. The membranes were blocked (5% dry milk, 1×TBST; 0.1 M Tris-HCl, 0.5 M NaCl, 0.5% Tween20) for 1 h at room temperature, incubated with the primary affinity purified antibody diluted 1:500 in blocking buffer and washed in TBST. The secondary HRP-conjugated antibody (swine anti-rabbit immunoglobulin/HRP, DakoCytomation) was diluted 1:3000 in blocking buffer and chemiluminescence detection was carried out using a Chemidoc™ CCD camera (Bio-Rad Laboratories) and SuperSignal® West Dura Extended Duration substrate (Pierce), according to the manufacturer's protocol. The results are discussed below and presented in FIG. 2.

b) Results

The quality of polyclonal antibody preparations has proven to be dependent on the degree of stringency in the antibody purifications, and it has previously been shown that depletion of antibodies directed against epitopes not originated from the target protein is necessary to avoid cross-reactivity to other proteins and background binding (Agaton C et al (2004) J. Chromatogr. A 1043:33-40).

Thus, a protein microarray analysis was performed to ensure that mono-specific polyclonal antibodies of high specificity had been generated by depletion of antibodies directed against the $His_6$-tag as well as of antibodies against the ABP-tag. This was followed by affinity capture of antigen selective antibodies on an affinity column with immobilized antigen.

To quantify the amount of protein in each spot of the protein array, a two color dye labeling system was used, with a combination of primary and secondary antibodies. Tag-specific IgY antibodies generated in hen were detected with a secondary goat anti-hen antibody labeled with Alexa 555 fluorescent dye. The specific binding of the rabbit msAb to its antigen on the array was detected with a fluorescently Alexa 647 labeled goat anti-rabbit antibody. In FIG. 1, the array results are shown as bars corresponding to the amount of Alexa 647 fluorescence intensity (y axis) detected from each spot of the array. Each protein fragment is spotted in duplicates, and each bar on the x axis of the diagram represents one protein spot. The protein array analysis shows that the affinity purified mono-specific antibody against SATB2 is highly selective to the correct protein fragment and shows a very low background to all other protein fragments analyzed on the array.

The result of the Western blot analysis (FIG. 2) shows that the antibody specifically detects a single band of approximately 100 kDa in a bladder tumor cell line (RT-4), an ovary cystadenocarcinoma cell line (EFO-21) and an epidermoid cell line (A-431) (lanes 1-3). In addition, a weaker specific band is seen in liver and tonsil tissue samples (lanes 4-5). The theoretical molecular weight of SATB2 is 82 kDa (as calculated from the SATB2 amino acid sequence SEQ ID NO:2), corresponding well to the results obtained with account taken of the fact that the analyzed protein may be glycosylated or otherwise modified under the conditions of the analysis.

3) Tissue Profiling by Immunohistochemistry a) Material and Methods

In total, 576 paraffin cores containing human tissues were analyzed using the mono-specific antibody sample. All tissues used as donor blocks for tissue microarray (TMA) production were selected from the archives at the Department of Pathology, University Hospital, Uppsala, in agreement with approval from the local ethical committee. Corresponding tissue sections were examined to determine diagnosis and to select representative areas in donor blocks. Normal tissue was defined as microscopically normal (non-neoplastic) and was most often selected from specimens collected from the vicinity of surgically removed tumors. Cancer tissue was reviewed for diagnosis and classification. All tissues were formalin fixated, paraffin embedded, and sectioned for diagnostic purposes.

The TMA production was performed essentially as previously described (Kononen J et al (1998) Nature Med. 4:844-847; Kallioniemi O P et al (2001) Hum. Mol. Genet. 10:657-662). Briefly, a hole was made in the recipient TMA block. A cylindrical core tissue sample from the donor block was acquired and deposited in the recipient TMA block. This was repeated in an automated tissue arrayer from Beecher Instrument (ATA-27, Beecher Instruments, Sun Prairie, Calif., USA) until a complete TMA design was produced. TMA recipient blocks were baked at 42° C. for 2 h prior to sectioning.

The design of TMA:s was focused on obtaining samples from a large range of representative normal tissues, and on including representative cancer tissues. This has previously been described in detail in Kampf C et al (2004) Clin. Proteomics 1:285-300. In brief, samples from 48 normal tissues and from 20 of the most common cancer types affecting humans were selected. In total, eight different designs of TMA blocks, each containing 72 cores of tissue with 1 mm diameter, were produced. Two of the TMA:s represented normal tissues, corresponding to 48 different normal tissues in triplicates from different individuals. The remaining 6 TMA:s represented cancer tissue from 20 different types of cancer. For 17 of the 20 cancer types, 12 individually different tumors were sampled, and for the remaining 3 cancer types, 4 individually different tumors were sampled, all in duplicates from the same tumor. The TMA blocks were sectioned with 4 µm thickness using a waterfall microtome (Leica), and placed onto SuperFrost® (Roche Applied Science) glass slides for immunohistochemical analysis.

Automated immunohistochemistry was performed as previously described (Kampf C et al (2004) Clin. Proteomics 1:285-300). In brief, the glass slides were incubated for 45 min in 60° C., de-paraffinized in xylene (2×15 min) and hydrated in graded alcohols. For antigen retrieval, slides were immersed in TRS (Target Retrieval Solution, pH 6.0, DakoCytomation) and boiled for 4 min at 125° C. in a Decloaking Chamber® (Biocare Medical). Slides were placed in the Autostainer® (DakoCytomation) and endogenous peroxidase was initially blocked with $H_2O_2$ (DakoCytomation). The primary antibody and goat anti-rabbit peroxidase conjugated Envision® were incubated for 30 min each at room temperature. Between all steps, slides were rinsed in wash buffer (DakoCytomation). Finally, diaminobenzidine (DakoCytomation) was used as chromogen and Harris hematoxylin (Sigma-Aldrich) was used for counterstaining. The slides were mounted with Pertex® (Histolab).

All immunohistochemically stained sections from the eight different TMA:s were scanned using a ScanScope T2 automated slide-scanning systems (Aperio Technologies). In order to represent the total content of the eight TMA:s, 576 digital images were generated. Scanning was performed at 20 times magnification. Digital images were separated and extracted as individual tagged image file format (TIFF) files for storage of original data. In order to be able to handle the images in a web-based annotation system, the individual images were compressed from TIFF format into JPEG format. All images of immunohistochemically stained tissue were manually evaluated under the microscope and annotated by a board certified pathologist or by specially educated personnel (followed by verification of a pathologist). Annotation of each different normal and cancer tissue was performed using a simplified scheme for classification of immunohistochemical outcome. Each tissue was examined for representativity and immunoreactivity. The different tissue specific cell types included in each normal tissue type were annotated. For each cancer, tumor cells and stroma were annotated. Basic annotation parameters included an evaluation of i) staining intensity, ii) fraction of stained cells and iii) subcellular localization (nuclear and/or cytoplasmic/membranous). Staining intensity was subjectively evaluated in accordance to standards used in clinical histo-pathological diagnostics and outcome was classified as: negative=no immunoreactivity, weak=faint immunoreactivity, moderate=medium immunoreactivity or strong=distinct and strong immunoreactivity. The fraction of stained cells was classified as <2%, 2-25%, 26-75% or >75% immunoreactive cells of the representative cell population. Based on both the intensity and fraction of immunoreactive cells, a "staining score" was given for each tissue sample: 0=negative, 1=weak, 2=moderate and 3=strong.

b) Results

Figure 3A:
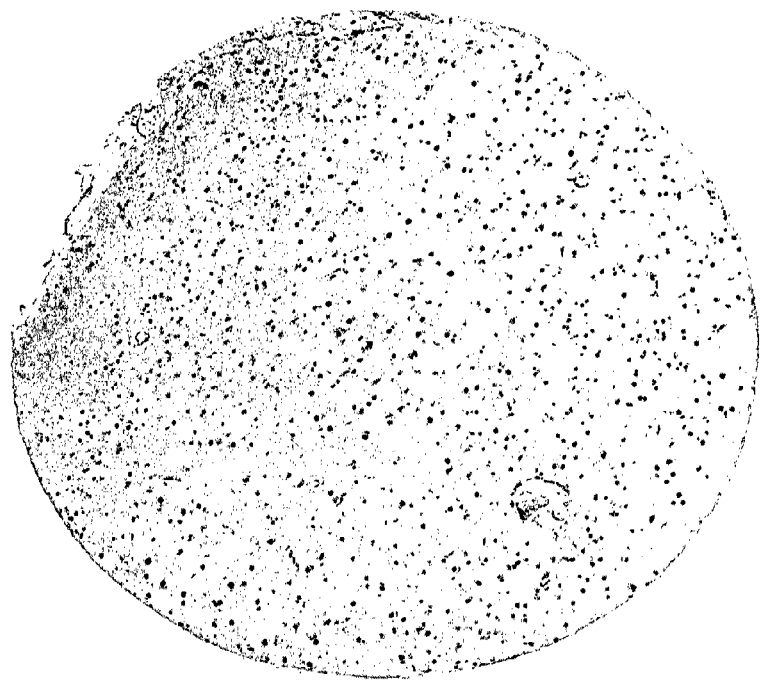
FIGS. 3A and 3B show immunohistochemical staining of SATB2 in the cell nuclei of (A) normal cerebral cortex and hippocampus and (B) normal testis.
Figure 3A:
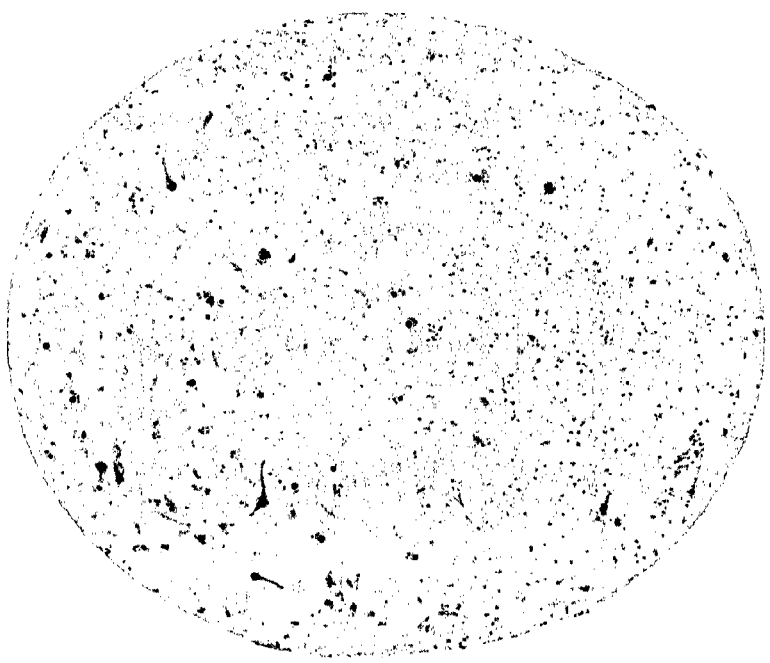
Figure 3B:
Figure 3C:
FIGS. 3C-3E show staining of SATB2 in glandular cells in mucosa of (C) appendix, (D) colon, and (E) rectum, all from normal subjects.
Figure 3D:
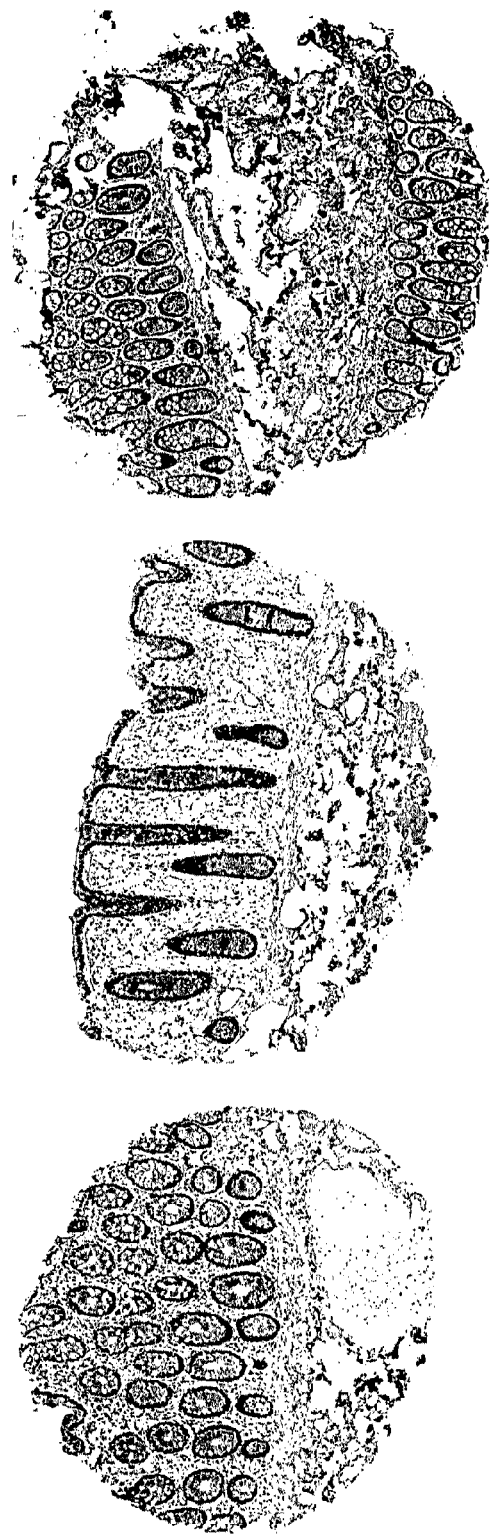
Figure 3E:
Figure 3F:
FIG. 3F shows a higher magnification of the staining in colonal mucosa.
Figure 4A:
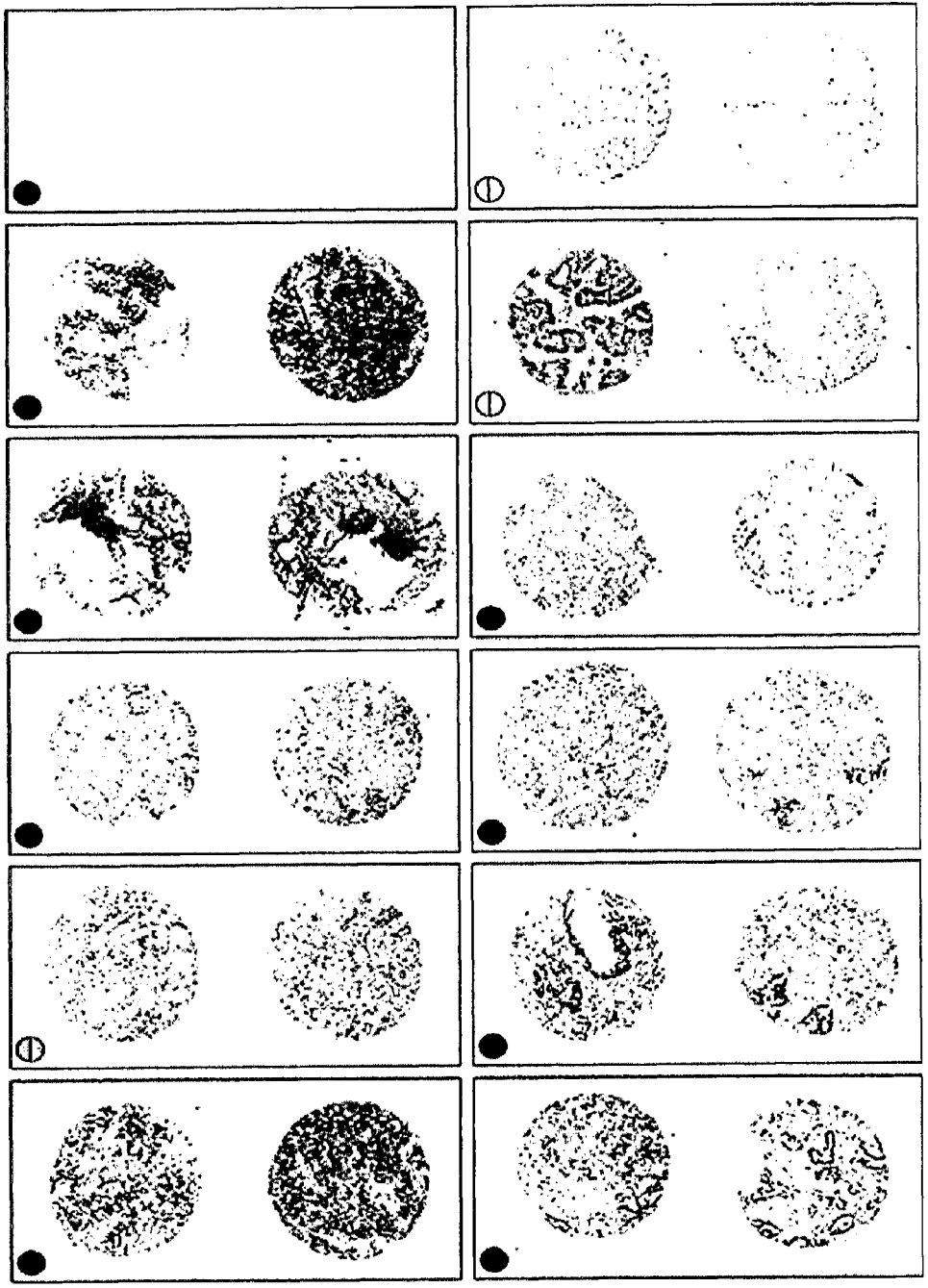
FIG. 4A shows immunohistochemical staining of SATB2 in all of eleven tested colo-rectal cancer samples (duplicates).
Figure 4B:
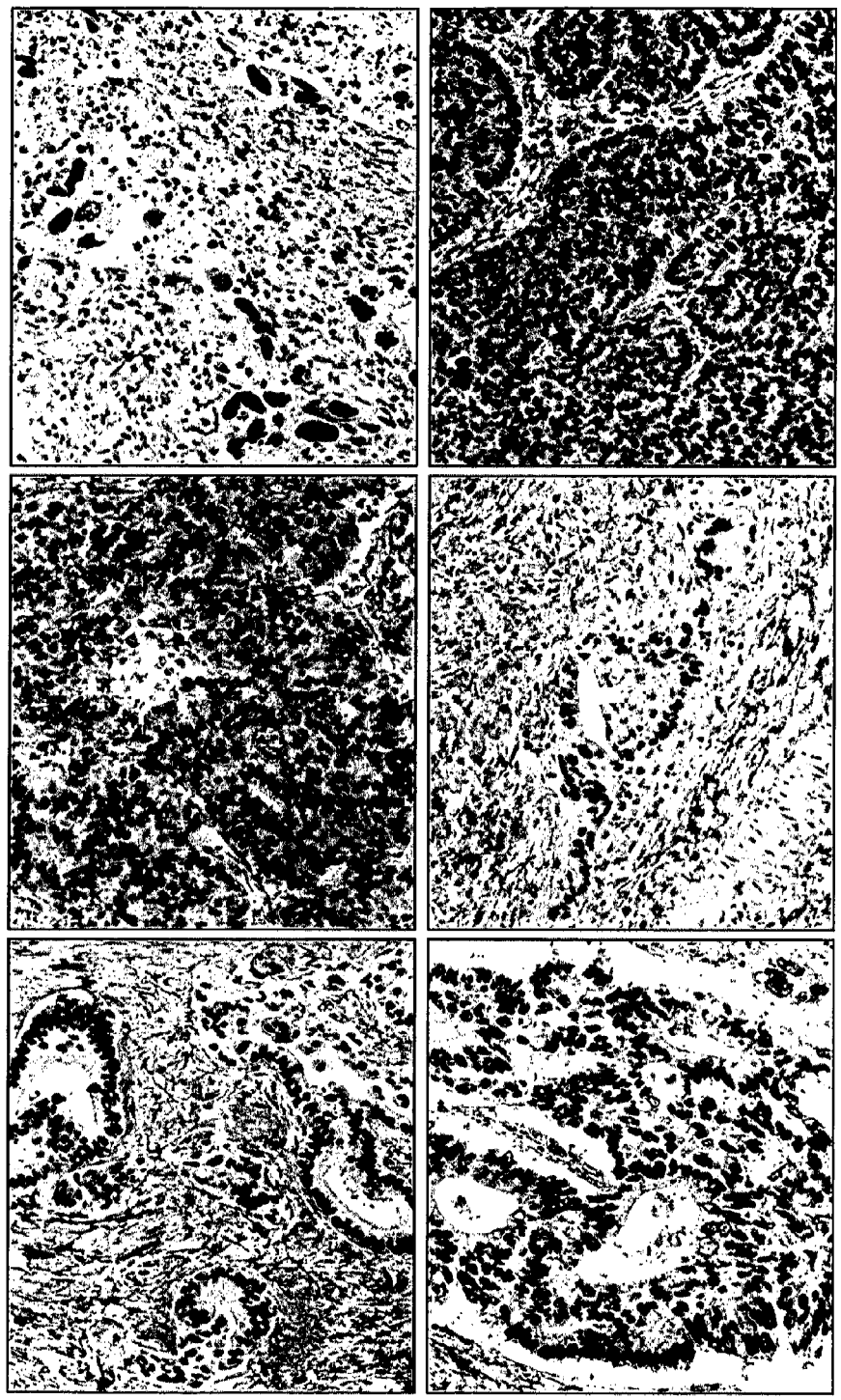
FIG. 4B shows a higher magnification of six of the cancer samples shown in FIG. 4A.

The results from tissue profiling with the mono-specific antibody generated towards a recombinant protein fragment of the human target protein SATB2 shows a particular immunoreactivity (dark grey) in several normal tissues and in colorectal cancer (Tables 1-4 and FIGS. 3-4).

Table 1 shows the SATB2 protein expression pattern in normal human tissues. Using immunohistochemistry and TMA technology, 144 spots (1 mm in diameter) representing 48 different types of normal tissue were screened for expression of SATB2. Table 1 shows the level of expression in the different tissues. Strong expression (staining score 3) was found in tissues from the distal GI-tract and in two areas of the brain. Moderate (staining score 2) levels of expression was detected in the testis and epididymis. Focal lymphoid cells showed moderate or weak (staining score 1) expression. All other cells and tissues were negative (staining score 0). N.R. means that no representative tissues were present. SATB2 is also expressed in some neuronal tissues and testis.

TABLE 1

Expression pattern of SATB2 in normal tissues

| Tissue type | Cell type | Staining score |
| --- | --- | --- |
| Adrenal gland | cortical cells | 0 |
|  | medullar cells | N.R. |
| Appendix | glandular cells | 3 |
|  | lymphoid tissue | 0 |
| Bone marrow | bone marrow poetic cells | 0 |
| Breast | glandular cells | 0 |
| Bronchus | surface epithelial cells | 0 |
| Cerebellum | cells in granular layer | 0 |
|  | cells in molecular layer | 0 |
|  | purkinje cells | 0 |
| Cerebral cortex | neuronal cells | 3 |
|  | non-neuronal cells | 0 |
| Cervix, uterine | glandular cells | 0 |
|  | surface epithelial cells (squamous) | N.R. |
| Colon | glandular cells | 3 |
| Duodenum | glandular cells | 0 |
| Endometrium 1 | cells in endometrial stroma/ECM | 0 |
|  | cells in myometrium/ECM | 0 |
|  | glandular cells | 0 |
| Endometrium 2 | cells in endometrial stroma/ECM | 0 |
|  | cells in myometrium/ECM | 0 |
|  | glandular cells | 0 |
| Epididymis | glandular cells | 2 |
| Esophagus | surface epithelial cells | 0 |
| Fallopian tube | glandular cells | 0 |
| Gall bladder | glandular cells | 0 |
| Heart muscle | myocytes | 0 |
| Hippocampus | neuronal cells | 3 |
|  | non-neuronal cells | 0 |
| Kidney | cells in glomeruli | 0 |
|  | cells in tubuli | 0 |
| Lateral ventricle | neuronal cells | 0 |
|  | non-neuronal cells | 0 |
| Liver | bile duct cells | 0 |
|  | hepatocytes | 0 |
| Lung | alveolar cells | 0 |
|  | macrophages | 0 |
| Lymph node | follicle cells (cortex) | 0 |
|  | non-follicle cells (paracortex) | 2 |
| Nasopharynx | surface epithelial cells | 0 |
| Oral mucosa | surface epithelial cells | 0 |
| Ovary | follicle cells | 0 |
|  | ovarian stromal cells | 0 |
| Pancreas | exocrine pancreas | 0 |
|  | islet cells | 0 |
| Parathyroid gland | glandular cells | 0 |
| Placenta | decidual cells | 0 |
|  | trophoblastic cells | 0 |
| Prostate | glandular cells | 0 |
| Rectum | glandular cells | 3 |
| Salivary gland | glandular cells | 0 |
| Seminal vescicle | glandular cells | 0 |
| Skeletal muscle | myocytes | 0 |
| Skin | adnexal cells | 0 |
|  | epidermal cells | 0 |
| Small intestine | glandular cells | 0 |
| Smooth muscle | smooth muscle cells | 0 |
| Soft tissue 1 | mesenchymal cells | 0 |

TABLE 1-continued

Expression pattern of SATB2 in normal tissues

| Tissue type | Cell type | Staining score |
|---|---|---|
| Soft tissue 2 | mesenchymal cells | 0 |
| Spleen | cells in red pulp | 0 |
|  | cells in white pulp | 0 |
| Stomach 1 | glandular cells | 0 |
| Stomach 2 | glandular cells | 0 |
| Testis | cells in ductus seminiferus | 2 |
|  | leydig cells | 0 |
| Thyroid gland | glandular cells | 0 |
| Tonsil | follicle cells (cortex) | 0 |
|  | non-follicle cells (paracortex) | 1 |
|  | surface epithelial cells | 0 |
| Urinary bladder | surface epithelial cells | 0 |
| Vagina | surface epithelial cells | 0 |
| Vulva/anal skin | surface epithelial cells | 0 |

FIG. 3A shows a microscopic enlargement, which exhibits nuclear positivity (dark grey) in neurons from cerebral cortex and hippocampus. Surrounding tissue and glial cells were negative (light grey). Tissue sections from testis showed a moderate and mainly nuclear positivity (dark grey) in the ductus seminiferous (FIG. 3B).

A specific finding in the histological array involving this invention was the distinct, strong nuclear positivity (dark grey) found in glandular cells of the mucosa in appendix (FIG. 3C), colon (3D) and rectum (3E). Note the negative staining (light grey) of other cell types, e.g. inflammatory cells, endothelial cells, also present in the mucosa. FIG. 3F shows two high power magnifications of the colonic mucosa showing that all glandular cells have strong nuclear expression (dark grey) of the SATB2 protein.

Table 2 shows the level of SATB2 expression in 216 different cancer tissues. All 11 colo-rectal carcinomas represented showed positivity, and in 8 of these the expression was strong. Low power microscopic magnifications with immunohistochemically stained tissue sections showing the analyzed 11 cases of colo-rectal carcinoma are shown in FIG. 4A, while high power magnifications of representative areas from six of the colo-rectal carcinomas are shown in 4B. A vast majority of the cancer cells showed strong nuclear staining (dark grey) indicating a high level of SATB2 expression as compared to the surrounding negative (light grey) tissue containing normal cells.

TABLE 2

Expression pattern of SATB2 in 20 cancer types

| Cancer type | Subject number | | | | | | | | | | | |
|---|---|---|---|---|---|---|---|---|---|---|---|---|
|  | 1 | 2 | 3 | 4 | 5 | 6 | 7 | 8 | 9 | 10 | 11 | 12 |
| Breast cancer | 1 | 0 | 0 | 0 | 0 | 0 | 0 | 0 | 0 | 0 | 0 | N.R. |
| Cervical cancer | 1 | 0 | 0 | 0 | 0 | 0 | 0 | 0 | 0 | 0 | 0 | 0 |
| Colo-rectal cancer | 3 | 3 | 3 | 3 | 3 | 3 | 3 | 3 | 2 | 1 | 1 | N.R. |
| Endometrial cancer | 0 | 0 | 0 | 0 | 0 | 0 | 0 | 0 | 0 | 0 | 0 | 0 |
| Head & neck cancer | 0 | 0 | 0 | 0 |  |  |  |  |  |  |  |  |
| Kidney cancer | 3 | 1 | 1 | 0 | 0 | 0 | 0 | 0 | 0 | 0 | 0 | N.R. |
| Liver cancer | 0 | 0 | 0 | 0 | 0 | 0 | 0 | 0 | 0 | 0 | 0 | 0 |
| Lung cancer | 2 | 0 | 0 | 0 | 0 | 0 | 0 | 0 | 0 | 0 | 0 | 0 |
| Malignant carcinoid | 0 | 0 | 0 | 0 |  |  |  |  |  |  |  |  |
| Malignant glioma | 2 | 1 | 0 | 0 | 0 | 0 | 0 | 0 | 0 | 0 | 0 | 0 |
| Malignant lymphoma | 0 | 0 | 0 | 0 | 0 | 0 | 0 | 0 | 0 | 0 | 0 | 0 |
| Malignant melanoma | 0 | 0 | 0 | 0 | 0 | 0 | 0 | 0 | 0 | N.R. | N.R. | N.R. |
| Ovarian cancer | 1 | 0 | 0 | 0 | 0 | 0 | 0 | 0 | 0 | 0 | 0 | 0 |
| Pancreatic cancer | 0 | 0 | 0 | 0 | 0 | 0 | 0 | 0 | 0 | 0 | 0 | N.R. |
| Prostate cancer | 1 | 0 | 0 | 0 | 0 | 0 | 0 | 0 | 0 | 0 | 0 | 0 |
| Skin cancer | 0 | 0 | 0 | 0 | 0 | 0 | 0 | 0 | 0 | 0 | 0 | 0 |
| Stomach cancer | 2 | 2 | 0 | 0 | 0 | 0 | 0 | 0 | 0 | 0 | 0 | 0 |
| Testis cancer | 2 | 1 | 0 | 0 | 0 | 0 | 0 | 0 | 0 | 0 | 0 | N.R. |
| Thyroid cancer | 0 | 0 | 0 | 0 |  |  |  |  |  |  |  |  |
| Urothelial cancer | 2 | 2 | 0 | 0 | 0 | 0 | 0 | 0 | 0 | 0 | 0 | N.R. |

4) Colo-Rectal Cancer TMA
a) Material and Methods

Archival formalin-fixed paraffin-embedded tissue from 122 patients (63 women and 59 men) diagnosed with colo-rectal carcinoma between 1999 and 2002 was collected from the Department of Pathology, Malmö University Hospital, Sweden. The median age of patients was 75 (32-88) years. 39 tumors were Dukes' stage A, 42 Dukes' stage B and 41 Dukes' stage C. Information regarding the date of death was obtained from the regional cause-of-death registries for all patients. Ethical permission was obtained from the Local Ethics Committee.

All 122 cases of colo-rectal carcinoma were histopathologically re-evaluated on slides stained with hematoxylin and eosin. TMA:s were then constructed by sampling 2×1.0 mm cores per case from areas representative of invasive cancer. The TMA:s were prepared and automated IMMUNOHISTOCHEMISTRY was performed as described in section 3 above, using the SATB2 antibody prepared as described in section 2 above.

Tissue annotation was essentially done as described in section 3 above, with the exception that staining intensity was considered either negative (no or faint immunoreactivity) or positive (moderate or strong reactivity). The fraction of cells exhibiting positive staining intensity in the cell nucleus was then calculated, yielding a value referred to as the "fraction score" for the sample. Thus, the "fraction score" corresponds to the percentage of cells in a sample that exhibits a positive staining intensity according to the definition in this section.

Based on the survival trends for all different strata, a dichotomized variable was constructed for further statistical analyses, defining a high/positive SATB2 expression as >25% positive nuclei and a low/negative SATB2 expression as <25% positive nuclei. Samples were then classified in two groups based on the fraction score, using 25% fraction score as the dividing criterion. Thus, no signal at all or a positive staining intensity in <25% of the cells in a tissue sample (core) classifies that sample in the group "<25%", whereas a positive staining intensity in >25% of the cells in a core classifies that sample in the group ">25%".

The above classification of samples was used for overall survival analysis according to the Kaplan-Meier estimator, and the log-rank test was used to compare survival in different strata. All statistical tests were two-sided, and p-values of <0.05% were considered significant. All calculations were made with the statistical package SPSS 12.0 (SPSS Inc. Illinois, USA).

b) Results

Figure 5:
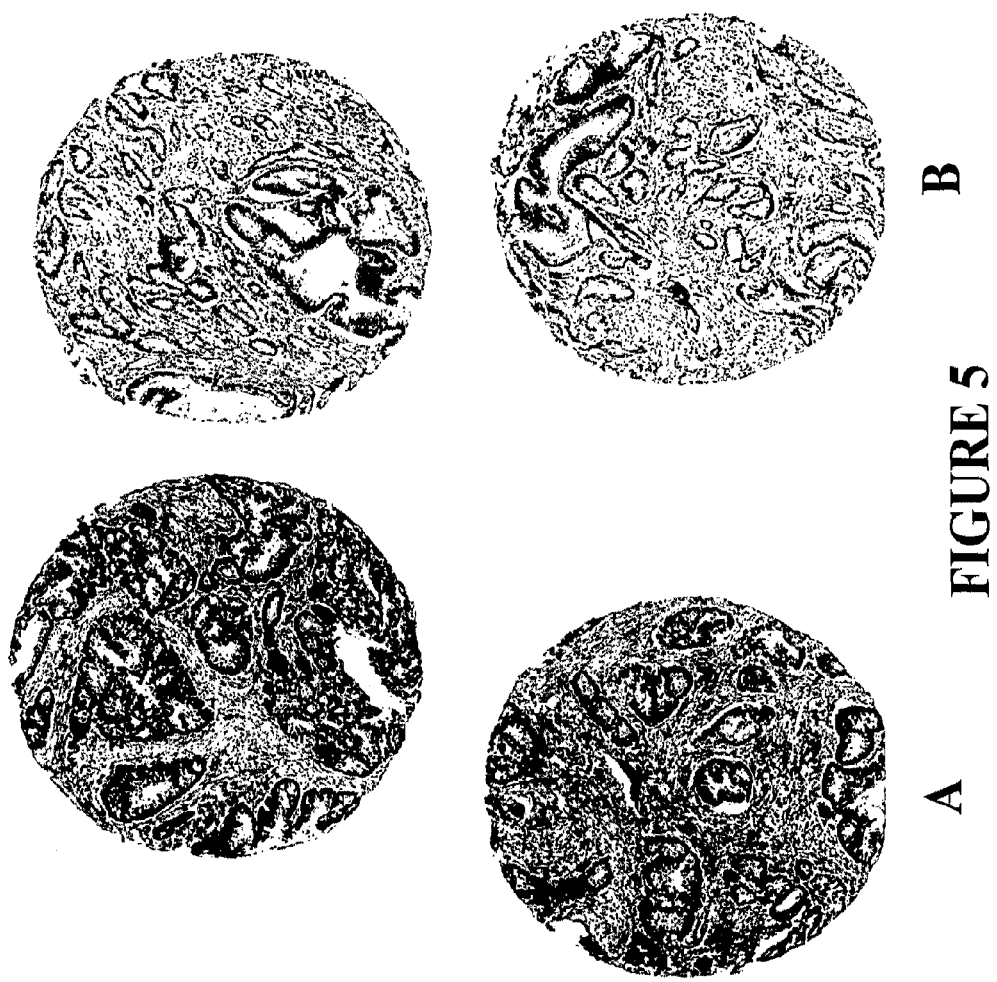
FIG. 5 shows immunohistochemical staining of intermediately differentiated colo-rectal adenocarcinoma.

Tissue microarray based analysis of 122 colo-rectal carcinomas showed that 99 tumors (81%) were positive for SATB2. Surprisingly, low or no expression of SATB2 was not possible to predict by routine sectioning and histochemical staining, as seen in FIG. 5. Both tumor samples (sections shown in duplicate) were diagnosed as intermediately differentiated colo-rectal adenocarcinoma. FIG. 5A shows a section with strong SATB2 expression, and in FIG. 5B, the sample lacks SATB2 expression.

Figures 6A, 6B:
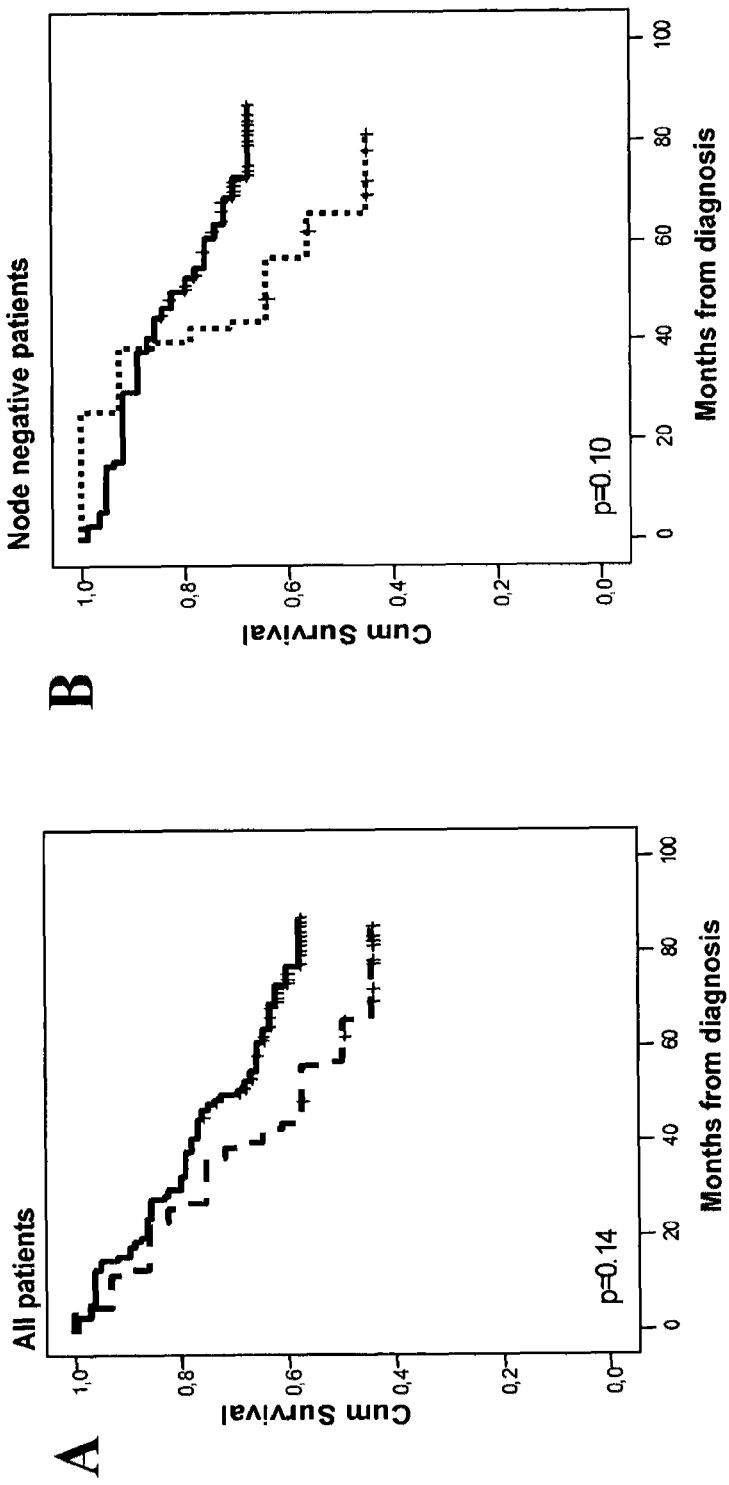
FIG. 6 shows the results of a survival analysis based on immunohistochemical staining of 122 subjects diagnosed with colo-rectal carcinomas. Tissue cores were scored for low or high SATB2 level. Solid lines: nuclear fraction >25%. Dashed/dotted lines: nuclear fraction <25%. Tissues from (A) all patients, (B) females only, (C) all node-negative patients, (D) node-negative females.
Figures 6C, 6D:
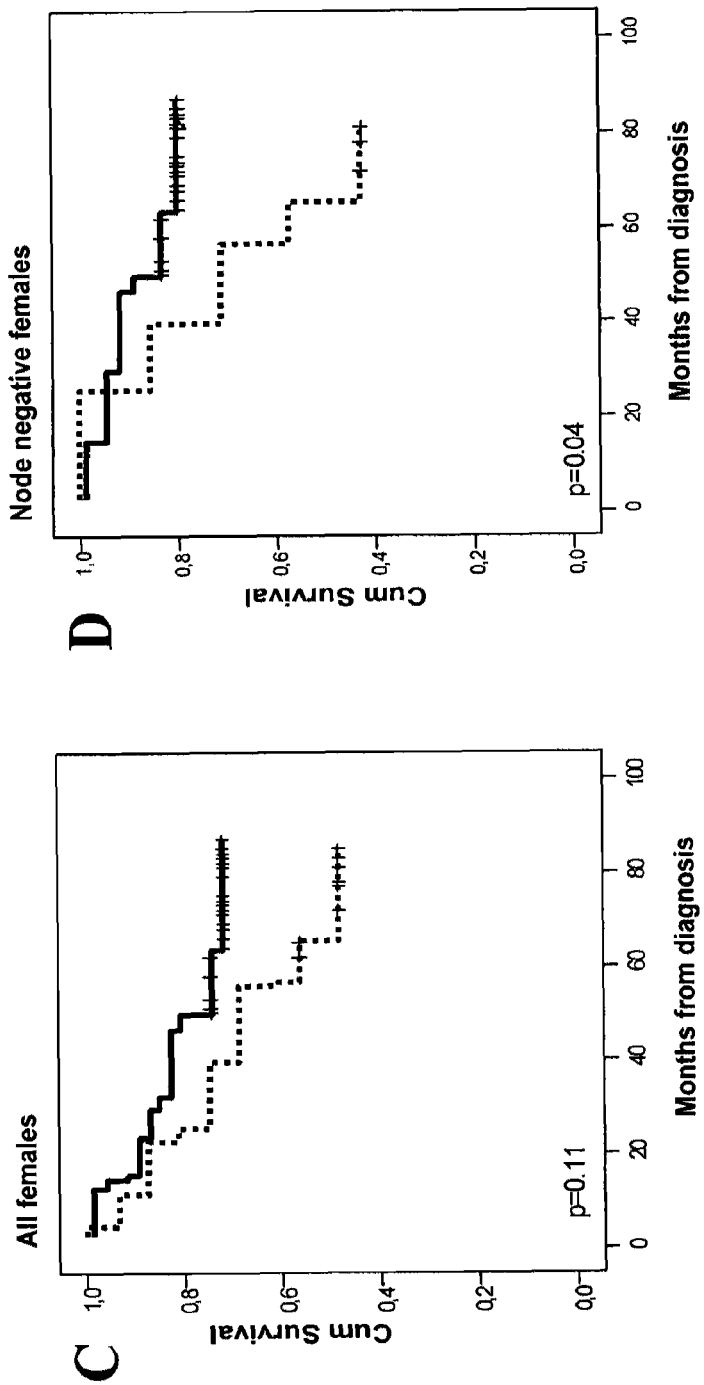

The results of the survival analysis are shown in FIG. 6, where the diagrams show the cumulative survival in different groupings of patients over time. Survival analysis based on the entire cohort revealed a trend (p=0.14) towards a shorter overall survival (OS) for patients having tumors with low SATB2 expression (FIG. 6A). The relationship between SATB2 expression and the clinicopathological variables sex and Dukes' stage was also examined. Female patients (n=63) having tumors with low SATB2 expression showed an increased trend (p=0.11) for even shorter OS compared to the whole cohort (FIG. 6B). FIG. 6C shows that a similar trend (p=0.10) was observed in node-negative (Dukes' stage A and B) patients (n=80). In the subgroup of node-negative women (n=44), this trend was significant (p=0.04) (FIG. 6D).

Another way to present the survival analysis data could be by using the "staining score" described in section 3 above. Then, samples scored as 0 and 1 would be defined as low SATB2 expression and samples scored as 2 and 3 would be defined as high SATB2 expression. A similar result as that seen in FIG. 6 is expected.

5) Quantitative Image Analysis of TMA Data

In order to obtain a quantitative expression measurement, the Aperio ScanScope CS Slide Scanner (Aperio Technologies, Vista, Calif., USA) system is used to capture digital images of the hybridized TMA slides prepared as described in section 4 above. Scanning is performed at 20 times magnification and images are stored as multilayered TIFF:s. These digital images are viewed using ImageScope (Aperio) and deemed suitable for analysis. The images are de-arrayed to visualize individual tissue cores using TMA Lab (Aperio). Initially, the Color Deconvolution algorithm (Aperio) is used to separate each image into three channels, i.e. red, green and blue (RGB). This enables each stain to be separately measured and thus makes it possible to subtract the hematoxylin counterstain from the diaminobenzidine chromogene staining.

Subsequently, a number of different algorithms are used to quantify nuclear, cytoplasmic or membranous staining. The IHC Nuclear algorithm (Aperio) is used to quantify nuclear staining of SATB2. Nuclei were identified based on intensity. Edges of the nuclei are identified using an edge threshold method, which automatically adjusts the threshold according to the mean of the edge pixels. A full description of all algorithms is available from Aperio Technologies. A pseudo-color mark-up image of each core on the TMA is generated and evaluated to confirm the accuracy of each algorithm.

The output values from the Nuclear algorithm are a percentage of positive nuclei and a nuclear RGB intensity value for each core on the TMA slide. An autoscore (AS) is calculated for the level of SATB2 expression on each tissue core, by multiplying the percentage positive nuclei by the nuclear RGB intensity for each core. AS analysis is made on cancer TMA samples, e.g. those described in section 4 above, and overall survival estimated according to Kaplan-Meier's method. The log-rank test is used to compare survival in different strata. Statistical calculations are made with the statistical package SPSS 12.0 (SPSS Inc. Illinois, USA).

6) Clustering Analysis
a) Material and Methods

In order to investigate the concordance in protein expression between known markers for colon cancer and SATB2, hierarchical clustering was performed. Clustering is a suitable method for evaluating trends and structures in data in initial mining steps. Groupings and categories that are not obvious by just browsing the data set can easily be detected by using unsupervised methods like hierarchical clustering. In life science, clustering has been used quite extensively in RNA transcriptional analysis, such as microarray data.

The 6 cancer TMA:s described in section 3 were used again, i.e. in total 216 cancer tissue samples. Besides the antibodies recognizing SATB2 prepared as per section 2 above, antibodies against the established markers CEA (DAKO, Glostrup, Denmark), CK20 (DAKO, Glostrup, Denmark), CDX2 (Novocastra, Newcastle upon Tyne, UK), p53 (DAKO, Glostrup, Denmark), Ki67 (DAKO, Glostrup, Denmark) and Cyclin B1 (Transduction laboratories, Lexington, USA) were tested using an automated IMMUNOHISTOCHEMISTRY method analogous to that described in section 3.

Pathologists annotated the TMA:s as presented in section 3 and gave a staining score to each core using a scale from 0-3, where 3 is a strong (black) staining and 0 is no (white) staining. Clustering was performed using the statistical computing language R. The clustering algorithm was used on the two dimensions of the data matrix, tissues and antibodies. In total, 7 antibodies and 216 tissues were used in the clustering procedure. Eight tissues were removed due to having no images that could quantify the expression levels. The clustering was made using a top-down hierarchical method with average agglomeration based on an Euclidian distance metric, where the distances between clusters are recomputed at each stage by the Lance-Williams dissimilarity update formula according to the average linkage. The algorithm used in the clustering orders the sub-trees so that the tighter cluster is displayed on the left hand side of each node.

To further study difference and similarities between SATB2 and CK20, IMMUNOHISTOCHEMISTRY analysis was made using the cancer TMA with 122 carcinoma cores described in section 4. TMA:s were stained with SATB2 antibody prepared as in section 2 and with CK20 antibody obtained from DAKO (Glostrup, Denmark). The two TMA:s were compared after being annotated according to the "fraction score" defined in section 4.

b) Results

Figure 7:
FIG. 7 shows the result of hierarchical clustering of expression data from 216 cancer tissues that were immunohistochemically stained for SATB2 expression and for expression of the conventional colon cancer markers CEA, CK20, CDX2, p53, Ki67 and Cyclin B1 (CCNB1).

The specificity of SATB2 as a marker for colo-rectal carcinoma as compared to the established markers CEA, CK20, CDX2, p53, Ki67 and Cyclin B1 was examined in 216 different tumors. Hierarchical clustering of data from expression profiles of these 7 different proteins resulted in the heatmap and accompanying dendrograms shown in FIG. 7. From the heatmap and dendrogram of tumors, it is clear that a vast majority of colo-rectal carcinomas form a cluster that is separated at the highest level based on high expression levels of SATB2, CK20, CDX2 and CEA. Further, the analysis shows that SATB2 clusters together with the CK20 and CDX2 cluster, all having a more specific expression than other tested markers that showed a more general expression pattern. In the cluster of 8 colo-rectal carcinomas, there was also one cervical adenocarcinoma and one case of cholangiocellular liver carcinoma that were strongly positive for SATB2. Outside of this cluster, there were three colo-rectal carcinomas negative for SATB2. Interestingly, the SATB2 expression pattern is not clearly correlated to the expression of CK20, and could therefore function as a complement to CK20 during characterization of colo-rectal cancer.

SATB2 and CK20 were analyzed in more detail on the 122 carcinoma TMA described in section 4. CK20 alone confirmed 86% (105/122) and SATB2 alone confirmed 81% (99/122) of the 122 colo-rectal carcinomas with a fraction score of >25% (FIG. 8). Interestingly, by combining the data from staining for both markers, 93% (113/122) of the colo-rectal cancers were clearly positive for one or both of the markers. Only 5 patients completely lacked expression of either CK20 or SATB2. This information is of interest when diagnosing a cancer and, more specifically, when trying to identify a metastasis, as a common clinical problem with cancer is patients that present a metastasis of unknown origin. Thus, by combining the information from both CK20 and SATB2, patients would more easily obtain an accurate diagnosis for colo-rectal adenocarcinoma.

Further, the SATB2 and CK20 expression in lymph node metastes from 17 patients with colo-rectal cancer was analyzed. CK20 alone confirmed the origin of 88% (15/17) of the metastases with a staining score of 2 or 3. SATB2 alone confirmed the origin of 82% (14/17) of the metastases with a fraction score of >25% (FIG. 9). Combining the data from staining for both markers, the origin of 94% (16/17) of the metastases was confirmed. This further supports that information regarding both SATB2 and CK20 expression is desirable when determining if a metastasis originates from a colo-rectal cancer.

Itemized Listing of Embodiments of the Invention

The following is a non-limiting and itemized listing of embodiments of the invention, presented for the purpose of providing further information regarding the various features and combinations provided by the invention in certain of its aspects.

1. Method for the diagnosis of colo-rectal cancer, comprising a step of detecting an SATB2 protein.

2. Method according to item 1, wherein the amino acid sequence of the SATB2 protein comprises a sequence selected from:
 i) SEQ ID NO:1; and
 ii) a sequence which is at least 85% identical to SEQ ID NO:1.

3. Method according to any preceding item, wherein the amino acid sequence of the SATB2 protein comprises a sequence selected from:
 i) SEQ ID NO:2; and
 ii) a sequence which is at least 85% identical to SEQ ID NO:2.

4. Method according to any preceding item, comprising the steps of:
 a) providing a sample from a patient suspected of having colo-rectal cancer;
 b) applying to the sample a detectable affinity ligand capable of selective interaction with the SATB2 protein to be detected, said application being performed under conditions that enable binding of the affinity ligand to any SATB2 protein present in the sample;
 c) removing non-bound affinity ligand; and
 d) detecting any affinity ligand remaining in association with the sample.

5. Method according to item 4, in which the sample is a body fluid sample.

6. Method according to item 5, in which the body fluid is selected from the group consisting of blood, plasma, serum, cerebral fluid, urine, semen and exudate.

7. Method according to item 4, in which the sample is a stool sample.

8. Method according to item 4, in which the sample is a tissue sample.

9. Method according to item 4, in which the sample is a cytology sample.

10. Method according to any one of items 4-9, wherein the detectable affinity ligand is selected from the group consisting of antibodies, fragments thereof and derivatives thereof.

11. Method according to any one of items 4-9, wherein the detectable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

12. Method according to any one of items 4-9, wherein the detectable affinity ligand is an oligonucleotide molecule.

13. Method according to any one of items 4-12, wherein the detectable affinity ligand comprises a label selected from the group consisting of fluorescent dyes and metals, chromophoric dyes, chemiluminescent compounds and bioluminescent proteins, enzymes, radioisotopes and particles.

14. Method according to any one of items 4-12, in which said detectable affinity ligand is detected using a secondary affinity ligand capable of recognizing the detectable affinity ligand.

15. Method according to item 14, in which said secondary affinity ligand capable of recognizing the detectable affinity ligand comprises a label selected from the group consisting of fluorescent dyes and metals, chromophoric dyes, chemiluminescent compounds and bioluminescent proteins, enzymes, radioisotopes and particles.

16. Kit for carrying out the method according to any one of items 1-15, which comprises
   a) a detectable affinity ligand capable of selective interaction with an SATB2 protein; and
   b) reagents necessary for detecting the presence of the affinity ligand.

17. Kit according to item 16, in which the detectable affinity ligand is selected from the group consisting of antibodies, fragments thereof and derivatives thereof.

18. Kit according to item 16, in which the detectable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

19. Kit according to item 16, wherein the detectable affinity ligand is an oligonucleotide molecule.

20. Kit according to any one of items 16-19, in which the detectable affinity ligand comprises a label selected from the group consisting of fluorescent dyes and metals, chromophoric dyes, chemiluminescent compounds and bioluminescent proteins, enzymes, radioisotopes and particles.

21. Kit according to any one of items 16-19, in which said reagents necessary for detecting the presence of the affinity ligand comprise a secondary affinity ligand capable of recognizing the detectable affinity ligand.

22. Kit according to item 21, in which said secondary affinity ligand capable of recognizing the detectable affinity ligand comprises a label selected from the group consisting of fluorescent dyes or metals, chromophoric dyes, chemiluminescent compounds and bioluminescent proteins, enzymes, radioisotopes and particles.

23. Use of an SATB2 protein as a diagnostic marker for colo-rectal cancer.

24. Use of an SATB2 protein, or an antigenically active fragment thereof, in the manufacture of a diagnostic agent for the diagnosis of colo-rectal cancer.

25. Use according any one of items 23 and 24, wherein the amino acid sequence of the SATB2 protein comprises a sequence selected from:
   i) SEQ ID NO:1; and
   ii) a sequence which is at least 85% identical to SEQ ID NO:1.

26. Use according any one of items 23 and 24, wherein the amino acid sequence of the SATB2 protein comprises a sequence selected from:
   i) SEQ ID NO:2; and
   ii) a sequence which is at least 85% identical to SEQ ID NO:2.

27. Affinity ligand capable of selective interaction with an SATB2 protein, which is an antibody or a fragment or a derivative thereof.

28. Affinity ligand according to item 27, which is obtainable by a process comprising a step of immunizing an animal with a protein whose amino acid sequence comprises the sequence SEQ ID NO:1.

29. Use of an affinity ligand according to any one of items 27-28 as a diagnostic agent.

30. Use of an affinity ligand according to any one of items 27-28 in the manufacture of a diagnostic agent for the diagnosis of colo-rectal cancer.

The invention claimed is:

1. A method for determining whether a mammalian subject having or suspected of having colo-rectal cancer has a shorter expected survival time as compared to a reference expected survival time, comprising the steps of:
   a) quantifying the amount of special AT-rich sequence binding protein 2 (SATB2 protein) present in a sample from the subject to yield a sample value;
   b) comparing the sample value obtained in step a) with a reference value of SATB2 protein that corresponds to said reference expected survival time; and
   c) determining that said subject has a shorter expected survival time as compared to said-reference expected survival time when the sample value is lower than said reference value.

2. The method according to claim 1, wherein the shorter expected survival time corresponds to a likelihood of five-year survival of 65% or lower.

3. The method according to claim 2, wherein the shorter expected survival time corresponds to a likelihood of five-year survival of 60% or lower.

4. The method according to claim 1, wherein said colo-rectal cancer is node-negative.

5. The method according to claim 1, wherein said colo-rectal cancer is in Dukes' stage A or B.

6. The method according to claim 1, wherein said colo-rectal cancer is colo-rectal adenoma.

7. The method according to claim 1, wherein said colo-rectal cancer is colo-rectal carcinoma.

8. The method according to claim 1, wherein said colo-rectal cancer is metastasizing.

9. The method according to claim 1, wherein said colo-rectal cancer is in Dukes' stage C.

10. The method according to claim 1, wherein said reference value is a predetermined value corresponding to the amount of SATB2 expression in a reference sample.

11. The method according to claim 1, wherein said reference value is a fraction score of 50% SATB2 positive cells.

12. The method according to claim 1, wherein said reference value is a fraction score of 25% SATB2 positive cells.

13. The method according to claim 1, wherein said reference value is a SATB2 expression autoscore value of 70.

14. The method according to claim 1, wherein said reference value is a SATB2 expression autoscore value of 50.

15. The method according to claim 1, in which the sample is a body fluid sample or a stool sample.

16. The method according to claim 1, in which the sample is a colo-rectal tissue sample.

17. The method according to claim 1, wherein the SATB2 protein comprises the amino acid sequence of SEQ ID NO:1.

18. The method according to claim 1, wherein the SATB2 protein comprises the amino acid sequence of SEQ ID NO:2.

19. The method according to claim 1, wherein step a) comprises:
   a1) applying to the sample a quantifiable affinity ligand that binds the SATB2 protein to be quantified, said application being performed under conditions that enable binding of the affinity ligand to any SATB2 protein present in the sample;

a2) removing non-bound affinity ligand; and a3) quantifying any affinity ligand bound to SATB2 protein in the sample.

20. The method according to claim 19, wherein the quantifiable affinity ligand is selected from the group consisting of antibodies, fragments thereof and derivatives thereof.

21. The method according to claim 19, wherein the quantifiable affinity ligand is a protein ligand derived from a scaffold selected from the group consisting of staphylococcal protein A and domains thereof, lipocalins, ankyrin repeat domains, cellulose binding domains, γ crystallines, green fluorescent protein, human cytotoxic T lymphocyte-associated antigen 4, protease inhibitors, PDZ domains, peptide aptamers, staphylococcal nuclease, tendamistats, fibronectin type III domain and zinc fingers.

22. The method according to claim 19, wherein the quantifiable affinity ligand is an oligonucleotide molecule.

23. The method according to claim 19, wherein the quantifiable affinity ligand comprises a label selected from the group consisting of fluorescent dyes and metals, chromophoric dyes, chemiluminescent compounds and bioluminescent proteins, enzymes, radioisotopes and particles.

24. The method according to claim 19, in which said quantifiable affinity ligand is detected using a secondary affinity ligand that binds the quantifiable affinity ligand.

25. The method according to claim 24, in which said secondary affinity ligand that binds the quantifiable affinity ligand comprises a label selected from the group consisting of fluorescent dyes and metals, chromophoric dyes, chemiluminescent compounds and bioluminescent proteins, enzymes, radioisotopes and particles.

26. A method for determining whether a mammalian subject having or suspected of having colo-rectal cancer has a longer expected survival time as compared to a reference expected survival time, comprising the steps of:
  a) quantifying the amount of special AT-rich sequence binding protein 2 (SATB2 protein) present in a sample from the subject to yield a sample value;
  b) comparing the sample value obtained in step a) with a reference value of SATB2 protein that corresponds to said reference expected survival time; and
  c) determining that said subject has a longer expected survival time as compared to said-reference expected survival time when the sample value is higher than said reference value.

* * * * *